United States Patent
Alroy et al.

(10) Patent No.: US 11,085,045 B2
(45) Date of Patent: Aug. 10, 2021

(54) FUNCTIONAL TRNA-APTAMER MOLECULES

(71) Applicants: ANIMA BIOTECH INC., Bernardsville, NJ (US); THOMAS JEFFERSON UNIVERSITY, Philadelphia, PA (US)

(72) Inventors: Iris Alroy, Ness Ziona (IL); Ya-Ming Hou, Philadelphia, PA (US); Howard Gamper, Philadelphia, PA (US)

(73) Assignees: Anima Biotech Inc., Bernardsville, NJ (US); Thomas Jefferson University, Philadelphia, PA (US)

( * ) Notice: Subject to any disclaimer, the term of this patent is extended or adjusted under 35 U.S.C. 154(b) by 253 days.

(21) Appl. No.: 15/773,271

(22) PCT Filed: Nov. 16, 2016

(86) PCT No.: PCT/IL2016/051232
§ 371 (c)(1),
(2) Date: May 3, 2018

(87) PCT Pub. No.: WO2017/085718
PCT Pub. Date: May 26, 2017

(65) Prior Publication Data
US 2018/0320183 A1  Nov. 8, 2018

Related U.S. Application Data

(60) Provisional application No. 62/256,149, filed on Nov. 17, 2015.

(51) Int. Cl.
*C12N 15/11* (2006.01)
*C12N 15/115* (2010.01)
*C12N 15/70* (2006.01)
*C12N 15/62* (2006.01)

(52) U.S. Cl.
CPC ............ *C12N 15/115* (2013.01); *C12N 15/62* (2013.01); *C12N 15/70* (2013.01); *C12N 2310/16* (2013.01); *C12N 2310/3517* (2013.01); *C12N 2310/3519* (2013.01); *C12N 2320/11* (2013.01)

(58) Field of Classification Search
None
See application file for complete search history.

(56) References Cited

U.S. PATENT DOCUMENTS

2006/0110796 A1* 5/2006 Schultz ............... C12N 9/93
435/69.1

FOREIGN PATENT DOCUMENTS

| WO | 2004050825 | 6/2004 | |
|---|---|---|---|
| WO | 2005116252 | 12/2005 | |
| WO | 2009002866 | 12/2008 | |
| WO | 2009047760 | 4/2009 | |
| WO | 2011036666 | 3/2011 | |
| WO | 2012011110 | 1/2012 | |
| WO | WO-2013016694 A2 * | 1/2013 | ........... C07D 233/04 |

OTHER PUBLICATIONS

Chaloin et al, Endogenous expression of a high-affinity pseudoknot RNA aptamer suppresses replication of HIV-1, Nucleic Acids Research, 2002, vol. 30, 18: 4001-4008 (Year: 2002).*
Paige et al., (2012) Fluorescence imaging of cellular metabolites with RNA. Science. Author manuscript; available in PMC Sep. 9, 2012. 3 pages.
Dolgosheina et al., (2014) RNA mango aptamer-fluorophore: a bright, high-affinity complex for RNA labeling and tracking. ACS chemical biology, 9(10), 2412-2420 (10 pages).
Filonov et al., (2014) Broccoli: rapid selection of an RNA mimic of green fluorescent protein by fluorescence-based selection and directed evolution. Journal of the American Chemical Society, 136(46), 16299-16308 (10 pages).
Gamper et al., (2015) Maintenance of protein synthesis reading frame by EF-P and m 1 G37-tRNA. Nature commmunications, 6, 7226, 1-13 (13 pages).
Kirchner & Ignatova, (2015) Emerging roles of tRNA in adaptive translation, signalling dynamics and disease. Nature Reviews Genetics, 16(2), 98-112 (16 pages).
Masuda et al., (2016) A genetically encoded fluorescent tRNA is active in live-cell protein synthesis. Nucleic acids research, 45(7), 4081-4093 and supplementary data (26 pages).
Paige et al., (2011) RNA mimics of green fluorescent protein. Science, 333(6042), 642-646 (6 pages).
Ponchon & Dardel, (2007) Recombinant RNA technology: the tRNA scaffold. Nature methods, 4(7), 571-576 (7 pages).
Sprinzl et al., (1998) Compilation of tRNA sequences and sequences of tRNA genes. Nucleic acids research, 26(1), 148-153 (6 pages).
Strack et al., (2013) A superfolding Spinach2 reveals the dynamic nature of trinucleotide repeat—containing RNA. Nature methods, 10(12), 1219, 1-9 (9 pages).
Suzuki et al., (2011) Human mitochondrial tRNAs: biogenesis, function, structural aspects, and diseases. Annual review of genetics, 45, 299-329 (33 pages).
Xiang et al., (2013) Crucial Optimization of Translational Components towards Efficient Incorporation of Unnatural Amino Acids into Proteins in Mammalian Cells. PloS one, 8(7), e67333, 1-7 (7 pages).

* cited by examiner

*Primary Examiner* — Ekaterina Poliakova-Georgantas
(74) *Attorney, Agent, or Firm* — Allan A. Fanucci

(57) ABSTRACT

The present invention provides functional aptamer-comprising tRNA molecules, useful in the study of tRNA and ribosomal activity.

20 Claims, 13 Drawing Sheets
Specification includes a Sequence Listing.

SEQUENCE LISTING

<160> NUMBER OF SEQ ID NOS: 6

<210> SEQ ID NO 1
<211> LENGTH: 98
<212> TYPE: DNA
<213> ORGANISM: Artificial Sequence
<220> FEATURE:
<223> OTHER INFORMATION: Spinach aptamer

<400> SEQUENCE: 1
gacgcgactg aatgaaatgg tgaaggacgg gtccaggtgt ggctgcttcg gcagtgcagc    60
ttgttgagta gagtgtgagc tccgtaacta gtcgcgtc                            98

<210> SEQ ID NO 2
<211> LENGTH: 95
<212> TYPE: DNA
<213> ORGANISM: Artificial Sequence
<220> FEATURE:
<223> OTHER INFORMATION: Spinach-2 aptamer

<400> SEQUENCE: 2
gatgtaactg aatgaaatgg tgaaggacgg gtccagtagg ctgcttcggc agcctacttg    60
ttgagtagag tgtgagctcc gtaactagtt acatc                               95

<210> SEQ ID NO 3
<211> LENGTH: 49
<212> TYPE: DNA
<213> ORGANISM: Artificial Sequence
<220> FEATURE:
<223> OTHER INFORMATION: Broccoli aptamer

<400> SEQUENCE: 3
gagacggtcg ggtccagata ttcgtatctg tcgactagag tgtgggctc                49

<210> SEQ ID NO 4
<211> LENGTH: 41
<212> TYPE: DNA
<213> ORGANISM: Artificial Sequence
<220> FEATURE:
<223> OTHER INFORMATION: Mango aptamer

<400> SEQUENCE: 4
ggaatataaa gaagggacgg tgcggagagg agatttatat t                        41

<210> SEQ ID NO 5
<211> LENGTH: 183
<212> TYPE: DNA
<213> ORGANISM: Artificial Sequence
<220> FEATURE:
<223> OTHER INFORMATION: V-Spinach tRNATyr/CUA

<400> SEQUENCE: 5
ggtggggttc ccgagcggcc aaagggagca gactctaaat ctgccgtcac gacgcgactg    60
aatgaaatgg tgaaggacgg gtccaggtgt ggctgcttcg gcagtgcagc ttgttgagta   120
gagtgtgagc tccgtaacta gtcgcgtcag acttcgaagg ttcgaatcct tcccccacca   180
cca                                                                 183

<210> SEQ ID NO 6
<211> LENGTH: 185
<212> TYPE: DNA
<213> ORGANISM: Artificial Sequence
<220> FEATURE:
<223> OTHER INFORMATION: V-Spinach tRNALeu/CAG -continued

```
<400> SEQUENCE: 6
gcgaaggtgg cggaattggt agacgcgcta gcttcaggtg ttagtgtcct tgacgcgact        60
gaatgaaatg gtgaaggacg ggtccaggtg tggctgcttc ggcagtgcag cttgttgagt       120
agagtgtgag ctccgtaact agtcgcgtca cggacgtggg ggttcaagtc cccccctcg        180 cacca                                                                   185
```

FUNCTIONAL TRNA-APTAMER MOLECULES

FIELD OF THE INVENTION

The present invention provides recombinant tRNA molecules and methods for their use in monitoring tRNA activity in-vivo. The recombinant tRNA may include fluorescent or conditionally-fluorescent tRNA molecules and methods for their use in monitoring tRNA activity in-vivo.

BACKGROUND OF THE INVENTION

A transfer ribonucleic acid (abbreviated tRNA) is a molecule composed of typically 70 to 90 ribonucleotides that serves as the link between the nucleotide sequence of nucleic acids (DNA and RNA) and the amino acid sequence of proteins. Its primary function is carrying a specific amino acid to the ribosome as directed by the three-nucleotide codon sequence in messenger RNA (abbreviated mRNA). As such, tRNAs are an essential component of protein translation, the biological synthesis of new proteins according to the genetic code.

Aptamers are oligonucleotide or peptide molecules that bind to a specific target molecule. Genetically encoded "Spinach" RNA is an aptamer capable of binding to, and turning on, a cell-permeable, non-toxic ligand, to emit GFP-like fluorescence (Paige, J. S. et al., Science, 2011, Vol. 333, pages 642-646). More recently aptamers such as "Broccoli" RNA (Filonov, G. S. et al., J. Am. Chem. Soc., 2014, Vol. 136, pages 16299-16308) and "Mango" RNA (Dolgosheina E. V. et al., ACS Chem. Biol., 2014, Vol. 9(10), pages 2412-2420) were successfully used in live-cell imaging of small molecules and metabolites. For example, the "Broccoli" aptamer ligated to the anticodon arm of a $tRNA^{LYS}$ was shown to stabilize the tRNA molecule in cells, yet, the resulting tRNA-aptamer fusion was non-functional in protein translation.

Use of donor-acceptor fluorophores to label two locations of a ribosome, or each of a ribosome and a tRNA, or each of a ribosome and an amino acid, for monitoring protein synthesis in cells or a cell-free translation systems are disclosed in WO 2004/050825, WO 2005/116252 and WO 2009/047760.

There remains a need for functional aptamer-incorporated tRNA molecules, and uses thereof for the study of protein synthesis, tRNA function and ribosomal activity among others.

SUMMARY OF THE INVENTION

The present invention provides a functionally active, recombinant tRNA comprising an aptamer (or more) fused to tRNA, having the advantages of retaining tRNA functionality thus enabling broad spectrum of applications to all cells and organisms amenable to genetic engineering. As exemplified herein below, the aptamer-tRNAs fusion molecules disclosed herein are active in protein synthesis in *E. Coli* and eukaryotic cells at a rate that supports cell viability. Surprisingly, normal protein synthesis activities are performed even though the aptamer is large relative to tRNA (e.g. Spinach: 98 nucleotides; tRNA: 70-90 nucleotides) and despite the fact that both have well-defined tertiary structures. The results obtained using the aptamer-tRNAs disclosed herein indicate that the aptamer-tRNAs provide sensitive reporters for all aspects of tRNA life-cycle, including production, function and degradation. Given that tRNA is known to participate in a broad range of biological processes within the cell, the reporter-tRNA provided herein may be used to monitor numerous activities related to protein synthesis, including physiological disorders such as cellular stress and disease states, and many additional functions and activities. Since translation is the main function for tRNA, the aptamer-tRNA molecules disclosed herein provide new probes for live-cell imaging of protein synthesis in real time.

The present invention provides, in one aspect, a recombinant transfer RNA (tRNA) molecule, comprising an acceptor stem, a D stem, an anticodon arm, a T stem, and at least one aptamer.

In some embodiments, the aptamer comprises a target-binding module, wherein the target-binding module is capable of binding to a target ligand.

In some embodiments, the aptamer further comprises a transducer module, functionally linking the target-binding module to a ligand-binding module within said aptamer.

In some embodiments, the tRNA molecule comprises at least one of a D arm, a V loop, and a T arm.

In some embodiments, the tRNA molecule comprises a D arm and a T arm.

In some embodiments, the at least one aptamer is linked to the V loop of the tRNA, thereby forming V-aptamer-tRNA fusion molecule, also referred to as a recombinant tRNA molecule.

In some embodiments, the at least one aptamer is extending from the V loop of the tRNA, thereby forming the recombinant tRNA molecule disclosed herein In some embodiments, the acceptor stem comprises 5-11 bp, the D stem comprises 2-8 bp, the anticodon stem comprises 4-8 bp, the T stem comprises 2-7 bp, or any combination thereof.

In some embodiments, the acceptor stem comprises 7-9 bp, the D stem comprises 4-6 bp, the anticodon stem comprises six (6) bp, the T stem comprises 4-5 bp, or any combination thereof.

In some embodiments, the tRNA molecule is selected from the group consisting of tRNATyr, tRNALeu, tRNASer and tRNAMet. In some embodiments, the tRNA molecule is tRNATyr or tRNALeu.

In some embodiments, the tRNA molecule comprises the tRNA molecule tRNATyr.

In some embodiments, the recombinant tRNA molecule comprises the amino acid sequence set forth in SEQ ID NO: 5. In some embodiments, the recombinant tRNA molecule is consisting essentially the amino acid sequence set forth in SEQ ID NO: 5.

In some embodiments, the tRNA molecule comprises the tRNA molecule tRNALeu. In some embodiments, the recombinant tRNA molecule comprises the amino acid sequence set forth in SEQ ID NO: 6. In some embodiments, the recombinant tRNA molecule is consisting essentially the amino acid sequence set forth in SEQ ID NO: 6.

In some embodiments, the at least one aptamer is capable of binding to at least one signal-emitting ligand.

In some embodiments, the signal-emitting ligand emits a fluorescent signal.

In some embodiments, the aptamer comprises the oligonucleotide sequence set forth in any one of SEQ ID NO: 1, SEQ ID NO: 2, SEQ ID NO: 3, SEQ ID NO: 4 and derivatives thereof. Each possibility is a separate embodiment of the invention.

In some embodiments, the aptamer is consisting essentially the oligonucleotide sequence set forth in any one of SEQ ID NO: 1, SEQ ID NO: 2, SEQ ID NO: 3, SEQ ID NO:

4 and derivatives thereof. Each possibility is a separate embodiment of the invention.

In some embodiments, the aptamer comprises the oligonucleotide sequence set forth in SEQ ID NO: 2.

In some embodiments, the aptamer is consisting essentially the oligonucleotide sequence set forth in SEQ ID NO: 2. In some embodiments, the signal-emitting ligand is hydroxy benzylideneimidazolinone (HBI), a derivative of HBI, thiazole orange (TO), or a derivative of TO.

In some embodiments, the signal-emitting ligand is 3,5-difluoro-4-hydroxy benzylideneimidazolinone (DFHBI), DFHBI-1T, DFHBI-2T or TO1-Biotin.

In some embodiments, the tRNA molecule further comprises a CCA tail.

In some embodiments, the tRNA molecule further comprises an amino acid.

In some embodiments, the recombinant tRNA molecule comprises an amino acid and is capable of participating in effective translation.

In some embodiments, the tRNA molecule is derived from a eukaryotic tRNA molecule.

In some embodiments, the tRNA molecule is derived from a prokaryotic tRNA molecule.

In some embodiments, the tRNA molecule is bound to a ligand.

In some embodiments, the ligand is a signal-emitting ligand.

The present invention further provides, in another aspect, an oligonucleotide construct, comprising the sequence of any one of the recombinant tRNA molecules described above, or a complementary sequence thereof.

The present invention further provides, in another aspect, an expression vector, comprising: (i). a DNA oligonucleotide sequence encoding any one of the recombinant tRNA molecules described above; and (ii). a promoter operatively linked to the DNA oligonucleotide sequence.

In some embodiments, the promoter is a constitutive promotor.

In some embodiments, the promoter is an inducible promotor.

In some embodiments, the promoter is a eukaryotic promotor.

In some embodiments, the promoter is a prokaryotic promotor.

In some embodiments, the expression vector described above further comprises a polynucleotide sequence encoding at least one component selected from the group consisting of a negative regulatory control element, a positive regulatory control element, a transcriptional terminator, and a selection marker gene.

The present invention further provides, in another aspect, an eukaryotic cell, comprising any one of the recombinant tRNA molecules described above, any one of the oligonucleotide constructs described above, or any one of the expression vectors described above; wherein: (i) the eukaryotic cell is not a human cell; or (ii) the eukaryotic cell is an ex-vivo human cell.

The present invention further provides, in another aspect, a prokaryotic cell, comprising any one of the recombinant tRNA molecules described above, any one of the oligonucleotide constructs described above, or any one of the expression vectors described above.

In some embodiments, the prokaryotic cell is an E. Coli cell.

In some embodiments, the cell is a transgenic cell.

The present invention further provides, in another aspect, a method of monitoring a recombinant tRNA molecule, comprising the steps of:
(i) obtaining a recombinant tRNA molecule comprising an acceptor stem, a D stem, an anticodon arm, a T stem, and at least one aptamer, or an expression vector comprising:
 (a) a DNA oligonucleotide sequence encoding any one of the recombinant tRNA molecules described above; and
 (b) a promoter operatively linked to the DNA oligonucleotide sequence;
(ii) optionally, inducing expression of the recombinant tRNA molecule from the expression vector of step (i);
(iii) contacting the recombinant tRNA molecule of step (i) or step (ii) with a signal-emitting ligand capable of being bound by the aptamer of the tRNA molecule; and
(iv) monitoring the signal emitted by the signal-emitting ligand; thereby monitoring the recombinant RNA.

In some embodiments, the method further comprises the step of inducing the expression of the recombinant tRNA molecule from the expression vector.

In some embodiments, the method further comprises monitoring any one or more of the following: an interaction between the recombinant tRNA molecule and an additional molecule; ribosomal activity; mRNA translation; protein synthesis; stress response in a cell, tissue or organ; tRNA level; nucleoli localization in a cell; and a tRNA-related disease.

In some embodiments, the method further comprises monitoring an interaction between the recombinant tRNA molecule and an additional molecule.

In some embodiments, the method further comprises monitoring ribosomal activity.

In some embodiments, the method further comprises monitoring mRNA translation.

In some embodiments, the method further comprises monitoring protein synthesis.

In some embodiments, the method further comprises monitoring a stress response in a cell, tissue or organ.

In some embodiments, the method further comprises monitoring the level of tRNA.

In some embodiments, the method further comprises monitoring nucleoli localization in a cell.

In some embodiments, the method further comprises monitoring a tRNA-related disease.

In some embodiments, the tRNA-related disease is associated with mutations in tRNA genes; mutations in tRNA processing, charging and modification enzymes; or alterations in the tRNA pool.

In some embodiments, the tRNA-related disease is associated with mutations in tRNA genes.

In some embodiments, the tRNA-related disease is selected from the group consisting of combined oxidative phosphorylation defect (COXPD); mitochondrial encephalomyopathy, lactic acidosis and stroke-like episodes (MELAS); myoclonic epilepsy with ragged-red fibres (MERRF); cardiomyopathy; chronic ophthalmoplegia0; ragged-red fibres (RRFs); cataract, spastic paraparesis and ataxia; neonatal death; ataxia; myopathy; leigh syndrome; and hypertension.

In some embodiments, the tRNA-related disease is associated with mutations in tRNA processing, charging and modification enzymes.

In some embodiments, the tRNA-related disease is selected from the group consisting of type 2 diabetes mellitus; cancer; myopathy, lactic acidosis and sideroblastic anaemia (MLASA); Leukoencephalopathy with brain stem and spinal cord involvement and lactate elevation (LBSL);

recessive ataxia; myopathy and infantile Charcot-Marie-Tooth; intellectual disability; dubowitz syndrome; Charcot-Marie-Tooth syndrome; dominant intermediate Charcot-Marie-Tooth syndrome; pontocerebellar hypoplasia; and perrault syndrome.

In some embodiments, the tRNA-related disease is associated with alterations in the tRNA pool.

In some embodiments, the tRNA-related disease is selected from the group consisting of type 2 diabetes mellitus; cancer; Huntington disease; influenza infection; vaccinia infection; West Nile virus infection; Japanese encephalitis virus infection; and human immunodeficiency virus (HIV) infection.

In some embodiments, the method is performed in a cell.

In some embodiments, the cell is a eukaryote cell.

In some embodiments, the cell is a prokaryote cell.

In some embodiments, the method is carried out ex-vivo.

In some embodiments, the expression vector comprises a constitutive promoter.

In some embodiments, the expression vector comprises an inducible promoter, and the method further comprises the step of contacting the expression vector with a transcription-promoting ligand.

The present invention further provides, in another aspect, a non-human organism, comprising the any one of the recombinant tRNA molecule described above, any one of the oligonucleotide constructs described above, or any one of the expression vectors described above.

The present invention further provides, in another aspect, a transgenic non-human organism, comprising a gene encoding any one of the recombinant tRNA molecules described above.

In some embodiments, the gene is a genomic or nuclear gene.

In some embodiments, the gene is a mitochondrial gene.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

Exemplary embodiments are illustrated in referenced figures. It is intended that the embodiments and figures disclosed herein are to be considered illustrative rather than restrictive. The figures are listed below.

DETAILED DESCRIPTION

Figure 1A:
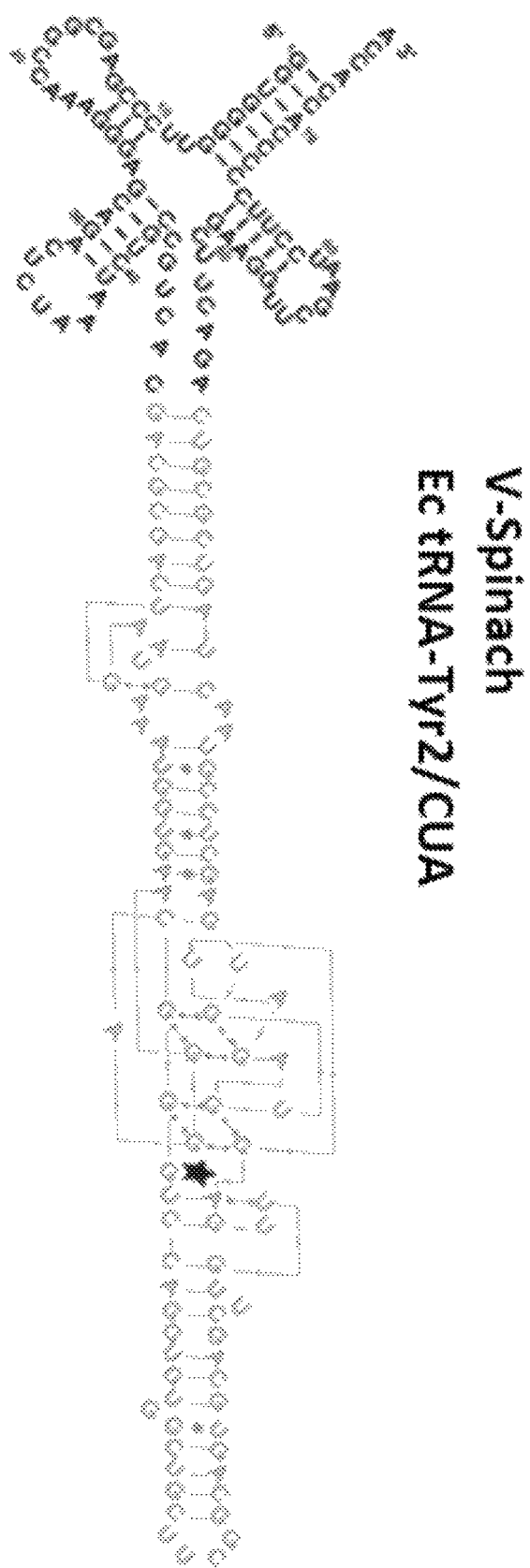
FIG. 1A exhibits sequence and secondary structure of Spinach to E.Coli tRNA$^{Tyr2}$ fusion in the V-loop (V-Spinach) (SEQ ID NO: 5), where the star indicates the bound ligand 3,5-difluoro-4-hydroxy benzylideneimidazolinone (DFHBI).

Provided herein, for the first time, genetically-engineered, functional, signal-emitting tRNA molecules. More specifically, provided herein are recombinant tRNA molecules, derived from human and bacterial natural tRNA molecules having fluorescently-labeled nucleic-acid aptamers incorporated therein, which maintain their translational activity in vivo.

The tRNA molecules provided herein are an important new addition to existing methods for imaging cellular components in general and the process of protein synthesis in particular, in live cells and whole organisms. Common current strategies include incorporating amino acid analogs into full-length proteins or incorporating puromycin derivatives into nascent polypeptide chains, followed by labeling these analogs or derivatives with a fluorophore through specific chemistry (e.g. "click chemistry"). The major drawbacks of these methods are that amino acid analogs are poorly incorporated into proteins due to discrimination by charging enzymes, and hence the biological activity of the protein is often compromised. More, puromycin derivatives have low cellular permeability and inevitably become cytotoxic over time. The aforementioned systems merely enable to measure protein accumulation, with poor temporal and spatial resolutions, and are not applicable for monitoring and evaluating the activity of the ribosomal synthesis process itself. Another known strategy takes advantage of the codon-specificity of tRNA during translation and has the versatility of creating a donor and an acceptor tRNA pair for FRET (fluorescence resonance energy transfer) imaging of protein synthesis on cognate di-codon mRNA sequences. The major drawback of this strategy, however, is that the fluorescent tRNA must be prepared ex-vivo and subsequently introduced into cells by transfection, encountering problems of low stoichiometry of ex-vivo labeling, contamination of one tRNA by another, and application only to cells that can be efficiently transfected (i.e. specific types of mammalian cells). Moreover, such an approach applies only to cell lines, precluding, for example, the labeling of whole organisms. The tRNA molecules provided herein address the limitations attributed to the aforementioned common strategies, because they are genetically encoded, quantitatively and specifically labeled upon their synthesis, and bind to cell-permeable and non-toxic ligands for fluorescence imaging. Advantageously, the expression of the modified tRNA molecules provided herein is promoter-dependent. Once expressed the tRNA is fully active in protein synthesis at a speed and efficiency sufficient to maintain cell viability during imaging. These and other benefits render the tRNA molecules of the invention applicable to all cells amenable to genetic engineering, thereby providing a broad impact in biology and biological research.

The term "fluorescent tRNA" as used herein also refers to conditionally-fluorescent tRNA, as it emits fluorescence upon an appropriate induction (condition).

A key feature of a genetically encoded fluorescent tRNA, or conditionally-fluorescent tRNA, for live-cell imaging of protein synthesis is that it must be specifically charged with the cognate amino acid, stably brought to the ribosome, and faithfully act as both an acceptor and a donor of peptidyl transfer. The tRNA molecules provided by the present invention meet all of these requirements, rendering them particularly useful for quantitative kinetic assays, as exemplified herein (e.g. Example 3). Surprisingly, and in contrast with what may have been expectable prior to the herein disclosed experiments, the modified tRNAs of the invention exhibit codon-anticodon pairing interaction upon entry to the ribosome A-site comparable with that exhibited by the corresponding naïve tRNA. Moreover, the tRNA molecules provided by the present invention demonstrate clear selectivity for the cognate codon in cell-based amber suppression assays (FIGS. 2B and 2D), indicating that they are fully accommodated by the ribosome. Considering the structural complexity and intricacy of the ribosome, and the extensive and dynamic interactions of the ribosome with the mRNA and tRNAs in successive rounds of peptide bond formation, the fact that the recombinant tRNA molecules disclosed herein are active in protein synthesis is highly unexpected.

Each nucleotide in RNA contains a ribose sugar, with carbons numbered 1' through 5'. A base is attached to the 1' position, in general, adenine (A), cytosine (C), guanine (G), or uracil (U), where adenine and guanine are purines, cytosine and uracil are pyrimidines. A phosphate group is attached to the 3' position of one ribose and the 5' position of the next. The phosphate groups have a negative charge each at physiological pH, making RNA a charged molecule (poly-anion).

RNA is transcribed with only four bases (adenine, cytosine, guanine and uracil), but these bases and attached sugars can be modified in numerous ways as the RNAs mature. Pseudouridine ($\Psi$), in which the linkage between uracil and ribose is changed from a C—N bond to a C—C bond, and ribothymidine (T) are found in various places (the most notable ones being in the T$\Psi$C loop of tRNA). Another notable modified base is hypoxanthine, a deaminated adenine base whose nucleoside is called inosine (I).

The structure of natural tRNAs consists of a primary structure (its sequence and modifications), a secondary structure (usually visualized as the cloverleaf structure), and a tertiary structure. All tRNAs have a similar L-shaped 3D structure that allows them to fit into the P and A sites of the ribosome. The cloverleaf structure becomes the 3D L-shaped structure through coaxial stacking of the helices, which is a common RNA tertiary structure motif. The lengths of each arm, as well as the loop 'diameter', in a tRNA molecule vary from species to species. A recent review summarizes tRNA biogenesis and structure, as well as emerging roles of tRNA in adaptive translation, signaling dynamics and disease (Kirchner and Ignatova, Nat. Rev. Genet., 2015, Vol. 16(2), pages 98-112).

tRNA primary structure comprises of the following components:
1. A 5'-terminal phosphate group, linked to the acceptor stem;
2. The acceptor stem is a 7- to 9-base pair (bp) stem made by the base pairing of the 5'-terminal nucleotide with the 3'-terminal nucleotide (which contains the CCA 3'-terminal group used to attach the amino acid), linked to the D arm. The acceptor stem may contain non-Watson-Crick base pairs;
3. The D arm is a 4- to 6-bp stem ending in a loop that often contains dihydrouridine (dihydrouridines are uridines modified by enzymes of the tRNA-dihydrouridine synthase (Dus) family), linked to the anticodon arm;
4. The anticodon arm is a 6-bp stem whose loop contains the anticodon, linked to the T arm. The tRNA 5'-to-3' primary structure contains the anticodon but in reverse order, since 3'-to-5' directionality is required to read the mRNA from 5'-to-3';

5. The T arm is a 4- to 5-bp stem containing the sequence TΨC where Ψ is pseudouridine, a modified uridine, linked to the acceptor stem optionally via a variable loop;
6. The CCA tail is a cytosine-cytosine-adenine sequence at the 3' end of the tRNA molecule, linked to the acceptor stem. The amino acid loaded onto the tRNA by aminoacyl tRNA synthetases, to form aminoacyl-tRNA, is covalently bonded to the 3'-hydroxyl group on the CCA tail. This sequence is important for the recognition of tRNA by enzymes and critical in translation. In prokaryotes, the CCA sequence is transcribed in some tRNA sequences. In most prokaryotic tRNAs and eukaryotic tRNAs, the CCA sequence is added during processing and is not a part of the tRNA gene.

Bases that have been modified, especially by methylation (e.g. tRNA (guanine-N7-)-methyltransferase), occur in several positions throughout the tRNA. The first anticodon base, or wobble-position, is sometimes modified to inosine (derived from adenine), pseudouridine or lysidine (derived from cytosine).

There is provided, in one aspect, a recombinant transfer RNA (tRNA) molecule, comprising an acceptor stem, a D stem, an anticodon arm, a T stem, and at least one aptamer.

The terms "recombinant transfer RNA molecule", "recombinant tRNA" and "modified tRNA" as used herein refer to a sequence essentially similar to that of a natural tRNA molecule, which includes the addition of a sequence of at least one aptamer. According to the principles of the present invention, the at least one aptamer in the recombinant tRNA molecules provided herein may replace, or be incorporated into, the acceptor stem, the D stem, the D loop, the V loop, the T stem, and/or the T loop. Preferably, the at least one aptamer in the recombinant tRNA molecules is not incorporated into the anticodon stem, the anticodon loop, and/or into the anticodon arm. Further, the ribonucleotide sequence of at least one aptamer in the recombinant tRNA molecules may be linked to the ribonucleotide sequences of the recombinant tRNA molecules provided herein directly, or via at least one linker ribonucleotide sequence(s). In some embodiments, the at least one linker ribonucleotide sequence comprises or consists of 1-20 ribonucleotides. In some embodiments, the at least one linker ribonucleotide sequence is consisting of two ribonucleotide sequences, wherein each ribonucleotide sequence comprises or consists of 1-20 ribonucleotides.

The term "acceptor stem" as used herein refers to a 5- to 11-base pair (bp) structure made by the base pairing of the 5'-terminal ribonucleotides with the 3'-terminal ribonucleotides of the tRNA sequence. The acceptor stem may contain non-Watson-Crick base pairs.

The term "D stem" as used herein refers to the 2- to 8-bp structure made by the base pairing of ribonucleotides of the tRNA sequence, found 0-5 bases 3' to the acceptor stem. The D stem may optionally be linked to a loop ("D loop") that often contains dihydrouridine.

The term "anticodon arm" as used herein refers to the 4- to 8-bp structure whose 1- to 10-base loop contains the anticodon, found 0-5 bases 3' to the D stem. The tRNA 5'-to-3' primary structure contains the anticodon but in reverse order, since 3'-to-5' directionality is required to read the mRNA from 5'-to-3'. It is to be understood that the term "anticodon arm" as used herein refers to the natural, unmodified, structure of the anticodon arm in natural tRNA molecules. In some embodiments, the anticodon arm consists of 5-50 ribonucleotides. In some embodiments, the anticodon arm consists of 5-40 ribonucleotides. In some embodiments, the anticodon arm consists of 5-30 ribonucleotides. In some embodiments, the anticodon arm consists of 5-20 ribonucleotides.

The terms "V loop" and "variable loop" as used herein are interchangeable and refer to a loop optionally located between the anticodon arm and the T stem. Commonly, the V loop includes at least 3 ribonucleotides, and no more than 20 ribonucleotides.

The term "T stem" as used herein refers to the 2- to 7-bp structure made by the base pairing of ribonucleotides of the tRNA sequence, found 0-5 bases 3' to the anticodon arm or to the V loop, if relevant. The T stem may optionally be linked to a loop ("T loop").

In some embodiments, the term "acceptor stem" refers to nucleotides 1-7 and 66-72 in a natural tRNA molecule. In some embodiments, the term "D stem" refers to nucleotides 10-13 and 22-25 in a natural tRNA molecule. In some embodiments, the term "anticodon arm" refers to nucleotides 27-43 in a natural tRNA molecule. In some embodiments, the term "V loop" refers to nucleotides 44-48 in a natural tRNA molecule. In some embodiments, the term "T stem" refers to nucleotides 49-52 and 61-65 in a natural tRNA molecule. In some embodiments, the term "acceptor stem" refers to nucleotides 1-7 and 66-72 in a natural tRNA molecule, the term "D stem" refers to nucleotides 10-13 and 22-25 in a natural tRNA molecule, the term "anticodon arm" refers to nucleotides 27-43 in a natural tRNA molecule, the term "V loop" refers to nucleotides 44-48 in a natural tRNA molecule, and the term "T stem" refers to nucleotides 49-52 and 61-65 in a natural tRNA molecule.

The term "stem-loop structure" is known to the skilled artisan and relates to a structure of a polynucleotide comprising a double-stranded region, preferably including the 5' end and the 3' end of the polynucleotide and/or regions of the polynucleotide close to said ends (the stem), as well as at least one single-stranded, i.e. non-base-paired region (the loop). It is understood that the loop may comprise base-paired, i.e. double-stranded, regions, as well.

The online tRNA database of the Bioinformatics unit in the University of Leipzig (http://www.bioinf.uni-leipzig.de/home.html) provides an alignment of tRNA molecules.

According to a different numbering method (Sprinzl et al., Nucleic Acids Research, 1998, Vol. 26(1), pages 148-153), a tRNA molecule includes 76 nucleotides (nucleotides 74-76 are CCA which are included in the tRNA genes in bacteria but not in Eukaryotes, in which they are added post transcription). Additional nucleotides are found and numbered as follows: (1) D loop (nucleotides 14-21): sometimes 3 additional nucleotides, numbered as 17a (located after 17), 20a and 20 b (located after 20); (2) Anticodon loop (nucleotide 32-38, no additional insertions); (3) Variable loop (nucleotides 44-46): variable length (4-23 nucleotides), not numbered as part of the 1-76: the nucleotides in the variable stem have the prefix 'e' and are located between position 45 and 46 obeying the base-pairing rules. The nucleotides in the 5'-strand and the 3'-strand are numbered by e11, e12, e13, ... and e21, e22, e23, ..., respectively; the second digit identifies the base-pair; and (4) T-loop (nucleotides 53-61, no insertions).

The term "aptamer" as used herein is well-known in the art, and generally means an oligonucleotide molecule sequence that binds, or is capable of binding, to a specific target molecule.

The term "capable of binding to a target molecule" as used herein refers to the ability of the aptamer to bind a specific target molecule under physiological conditions.

The term "physiological conditions" as used herein refers to internal or external conditions, preferably including temperature, pH, and solute concentration, corresponding to or mimicking conditions in a cell or in an organism.

In some embodiments, the aptamer comprises a target-binding module, wherein the target-binding module is capable of binding to a target ligand.

The term "target-binding module" as used herein refers to any ribonucleotide or ribonucleotide sequence in an aptamer which participates in the binding of a target ligand by the aptamer.

The term "capable of binding to a target ligand" as used herein refers to the ability of the target-binding module to bind a specific target ligand under physiological conditions.

The term "target ligand" as used herein refers to any ligand, which upon binding to the target-binding module stabilizes the ligand-binding module of the aptamer so the ligand-binding module becomes capable of binding to the ligand.

In some embodiments, the aptamer or the ligand-binding module of the aptamer are capable of binding, or are bound, to a signal-emitting ligand. The term "signal-emitting ligand" as used herein refers to a ligand which is capable of emitting a signal upon binding or while being bound to the aptamer or the ligand-binding module of the aptamer of the recombinant tRNA molecule of the present invention. In some embodiments, the ligand emits a signal only upon binding or while being bound to the aptamer or to the ligand-binding module of the aptamer of the recombinant tRNA molecule of the present invention, and does not emit a signal while unbound.

In some embodiments, the aptamer further comprises a transducer module, functionally linking the target-binding module to a ligand-binding module within said aptamer.

The term "transducer module" as used herein refers to two 1 to 20 ribonucleotide stretches, found between the ligand-binding module and the target-binding module, which upon binding of a target-ligand to the target-binding module stabilizes the ligand-binding module so the ligand-binding module becomes capable of binding to ligand.

The term "ligand-binding module" as used herein refers to any ribonucleotide or ribonucleotide sequence in an aptamer involved in binding the specific ligand of the aptamer.

The term "capable of emitting a signal" as used herein refers to the ability of the aptamer to emit a signal upon binding to a specific ligand, or while being bound to the specific ligand.

The term "upon binding" as used herein refers to the causative effect of an earlier event on a later event. For example, in embodiments in which the aptamer comprises a ligand-binding module but does not comprise a target binding module, a signal-emitting ligand would emit a signal only upon binding to the ligand-binding module. In other embodiments, in which the aptamer comprises a ligand-binding module and a target binding module, a signal-emitting ligand would emit a signal only upon binding of a target ligand to the target-binding module, and upon binding of the signal-emitting ligand to the ligand-binding module.

In some embodiments, the tRNA molecule comprises a D arm. In some embodiments, the tRNA molecule comprises a V loop. In some embodiments, the tRNA molecule comprises a T arm. In some embodiments, the tRNA molecule comprises a D arm and a T arm. In some embodiments, the tRNA molecule comprises an acceptor stem, a D arm, an anticodon arm, a signal-emitting aptamer and a T arm. In some embodiments, the tRNA molecule comprises an acceptor stem, a D arm, an anticodon arm, a signal-emitting aptamer and a T arm, wherein the signal-emitting aptamer is located between the anticodon arm and the T arm.

The term "D arm" as used herein refers to the structure formed from a D stem and a D loop.

The term "T arm" as used herein refers to the structure formed from a T stem and a T loop, containing the sequence TΨC where Ψ is pseudouridine, a modified uridine.

In some embodiments, the tRNA molecule comprises an acceptor stem, a D arm, an anticodon arm, a signal-emitting aptamer and a T arm, wherein the signal-emitting aptamer is located between the anticodon arm and the T arm, and wherein the tRNA molecule is a human tRNA molecule. In some embodiments, the tRNA molecule comprises an acceptor stem, a D arm, an anticodon arm, a signal-emitting aptamer and a T arm, wherein the signal-emitting aptamer is located between the anticodon arm and the T arm, and wherein the tRNA molecule is any human tRNA molecule. In some embodiments, the tRNA molecule is selected from the group consisting of $tRNA^{Leu}$, $tRNA^{Ser}$, $tRNA^{Lys}$ and $tRNA^{Tyr}$. Each possibility is a separate embodiment of the invention. Tables 1 and 2 provide a breakdown of currently-identified Human tRNA nuclear genes and *E. Coli* tRNA nuclear genes, respectively.

In some embodiments, the tRNA molecule comprises an acceptor stem, a D arm, an anticodon arm, a signal-emitting aptamer and a T arm, wherein the signal-emitting aptamer is located between the anticodon arm and the T arm, and wherein the tRNA molecule is a human tRNA molecule selected from the group consisting of $tRNA^{Leu/AAG}$, $tRNA^{Leu/CAA}$, $tRNA^{Leu/CAG}$, $tRNA^{Leu/TAA}$, $tRNA^{Leu/TAG}$, $tRNA^{Ser/AGA}$, $tRNA^{Ser/CGA}$, $tRNA^{Ser/GCT}$, $tRNA^{Ser/TGA}$, $tRNA^{Lys/TTT}$, and $tRNA^{Tyr/GTA}$. Each possibility is a separate embodiment of the invention.

In some embodiments, the tRNA molecule comprises an acceptor stem, a D arm, an anticodon arm, a signal-emitting aptamer and a T arm, wherein the signal-emitting aptamer is located between the anticodon arm and the T arm, and wherein the tRNA molecule is a human tRNA molecule selected from the group consisting of $tRNA^{Leu/AAG}$, $tRNA^{Leu/CAA}$, $tRNA^{Leu/CAG}$, $tRNA^{Leu/TAG}$, $tRNA^{Ser/CGA}$, $tRNA^{Ser/GCT}$ and $tRNA^{Ser/TGA}$. Each possibility represents a separate embodiment of the invention.

TABLE 1

| Human tRNA nuclear genes (513 genes) | | | |
|---|---|---|---|
| tRNA Isotype | Anticodon | No. of genes | V-loop length |
| Ala | AGC | 29 | 5 |
|  | CGC | 5 | 5 |
|  | TGC | 9 | 5 |
| Arg | ACG | 7 | 5 |
|  | CCG | 5 | 5 |
|  | CCT | 5 | 4-5 |
|  | TCG | 6 | 5 |
|  | TCT | 6 | 5 |
| Asn | ATT | 1 | 5 |
|  | GTT | 32 | 5 |
| Asp | GTC | 19 | 3-5 |
| Cys | GCA | 30 | 5 |
| Gln | CTG | 21 | 4 |
|  | TTG | 11 | 4 |
| Glu | CTC | 13 | 4 |
|  | TTC | 13 | 4 |

TABLE 1 -continued

Human tRNA nuclear genes (513 genes)

| tRNA Isotype | Anticodon | No. of genes | V-loop length |
|---|---|---|---|
| Gly | CCC | 7 | 4 |
| | GCC | 15 | 4 |
| | TCC | 9 | 4 |
| His | GTG | 11 | 4 |
| Ile | AAT | 14 | 5 |
| | GAT | 8 | 5 |
| | TAT | 5 | 5 |
| Leu | AAG | 12 | 10 |
| | CAA | 7 | 11-12 |
| | CAG | 10 | 11 |
| | TAA | 7 | 4 or 12 |
| | TAG | 3 | 10 |
| Lys | CTT | 17 | 5 |
| | TTT | 17 | 5 or 9 |
| Met | CAT | 20 | 5 |
| Phe | GAA | 12 | 5 |
| Pro | AGG | 10 | 5 |
| | CGG | 4 | 5 |
| | TGG | 7 | 5 |
| Ser | AGA | 12 | 5 or 11 |
| | CGA | 4 | 11 |
| | GCT | 8 | 11 |
| | TGA | 5 | 11 |
| Thr | AGT | 10 | 5 |
| | CGT | 6 | 5 |
| | TGT | 6 | 5 |
| Trp | CCA | 9 | 5 |
| Tyr | ATA | 1 | 5 |
| | GTA | 14 | 5 or 7 |
| Val | AAC | 11 | 5 |
| | CAC | 16 | 5 |
| | TAC | 5 | 5 |
| Stop | TCA | 3 | 5 or 9 |
| | CTA | 1 | 5 |
| | TTA | 2 | 5 |

TABLE 2

Escherichia Coli K12 tRNA genes (88 genes)

| tRNA Isotype | Anticodon | No. of genes | V-loop length |
|---|---|---|---|
| Ala | GGC | 2 | 5 |
| | TGC | 3 | 5 |
| Arg | ACG | 4 | 5 |
| | CCG | 1 | 5 |
| | CCT | 1 | 5 |
| | TCT | 1 | 5 |
| Asn | GTT | 4 | 5 |
| Asp | GTC | 3 | 5 |
| Cys | GCA | 1 | 4 |
| Gln | CTG | 2 | 5 |
| | TTG | 2 | 5 |
| Glu | TTC | 4 | 4 |
| Gly | CCC | 1 | 4 |
| | GCC | 4 | 5 |
| | TCC | 1 | 4 |
| His | GTG | 1 | 5 |
| Ile | GAT | 3 | 5 |
| Leu | GAG | 1 | 10 |
| | CAA | 1 | 10 |
| | CAG | 4 | 12 |
| | TAA | 1 | 10 |
| | TAG | 1 | 10 |
| Lys | TTT | 6 | 5 |
| Met | CAT | 8 | 5 |
| Phe | GAA | 2 | 5 |
| Pro | GGG | 1 | 5 |
| | CGG | 1 | 5 |
| | TGG | 1 | 5 |
| Ser | GGA | 2 | 14 |
| | CGA | 1 | 16 |
| | GCT | 1 | 18 |
| | TGA | 1 | 12 |
| Thr | GGT | 2 | 5 |
| | CGT | 2 | 5 |
| | TGT | 1 | 5 |
| Trp | CCA | 1 | 5 |
| Tyr | GTA | 3 | 10 |
| Stop | TCA | 1 | 5 |

In some embodiments, the tRNA molecule is a human tRNA molecule. In some embodiments, the tRNA molecule is a human tRNA molecule selected from the group consisting of tRNA$^{Leu}$, tRNA$^{Ser}$, tRNA$^{Lys}$, and tRNA$^{Tyr}$. Each possibility is a separate embodiment of the invention. In some embodiments, the tRNA molecule is a human tRNA molecule selected from the group consisting of tRNA$^{Leu/AAG}$, tRNA$^{Leu/CAA}$, tRNA$^{Leu/CAG}$, tRNA$^{Leu/TAA}$, tRNA$^{Leu/TAG}$, tRNA$^{Ser/AGA}$, tRNA$^{Ser/CGA}$, tRNA$^{Ser/GCT}$, tRNA$^{Ser/TGA}$, tRNA$^{Lys/TTT}$, and tRNA$^{Tyr/GTA}$. Each possibility is a separate embodiment of the invention.

In some embodiments, the tRNA molecule is a human tRNA molecule selected from the group consisting of tRNA$^{Leu/AAG}$, tRNA$^{Leu/CAA}$, tRNA$^{Leu/CAG}$, tRNA$^{Leu/TAG}$, tRNA$^{Ser/CGA}$, tRNA$^{Ser/GCT}$, and tRNA$^{Ser/TGA}$. Each possibility represents a separate embodiment of the invention.

In some embodiments, the recombinant tRNA comprises at least one aptamer fused to the V loop thereof. In some embodiments, the recombinant tRNA comprises one aptamer fused to the V loop thereof. In some embodiments, the recombinant tRNA comprises at least one aptamer fused to the V loop thereof, via a linker.

The term "fused to" is exchangeable with the terms "bound to", "linked to", "attached to", "extended from" and the like.

In some embodiments, the acceptor stem comprises 5-11 bp, the D stem comprises 2-8 bp, the anticodon stem comprises 4-8 bp, the T stem comprises 2-7 bp, or any combination thereof. In some embodiments, the acceptor stem comprises 5-11 bp, the D stem comprises 2-8 bp, the anticodon stem comprises 4-8 bp, and the T stem comprises 2-7 bp. In some embodiments, the acceptor stem comprises 7-9 bp, the D stem comprises 4-6 bp, the anticodon stem comprises 6 bp, the T stem comprises 4-5 bp, or any combination thereof. In some embodiments, the acceptor stem comprises 7-9 bp, the D stem comprises 4-6 bp, the anticodon stem comprises 6 bp, and the T stem comprises 4-5 bp.

In some embodiments, the tRNA molecule is selected from the group consisting of tRNA$^{Tyr}$, tRNA$^{Leu}$, tRNA$^{Ser}$ and tRNA$^{Met}$. In some embodiments, the tRNA molecule is tRNA$^{Tyr}$ or tRNA$^{Leu}$. In some embodiments, the tRNA molecule is tRNA$^{Tyr}$. In some embodiments, the tRNA molecule is tRNA$^{Leu}$.

In some embodiments, the at least one aptamer is capable of binding to at least one signal-emitting ligand. In some embodiments, the signal-emitting ligand emits a fluorescent signal. In some embodiments, the aptamer comprises the oligonucleotide sequence set forth in any one of SEQ ID NO: 1, SEQ ID NO: 2, SEQ ID NO: 3, SEQ ID NO: 4, a functional fragment thereof, and a functional homolog thereof. Each possibility represents a separate embodiment of the invention.

homolog has at least 90% identity to the original sequence, and maintains at least 70% of the activity of the original sequence. In some embodiments, the functional homolog has at least 90% identity to the original sequence, and maintains at least 90% of the activity of the original sequence.

In some embodiments, the aptamer comprises the oligonucleotide sequence set forth in SEQ ID NO: 2, a functional fragment thereof, or a functional homolog thereof. Each possibility represents a separate embodiment of the invention. In some embodiments, the aptamer comprises the oligonucleotide sequence set forth in SEQ ID NO: 2.

In certain embodiment, the aptamer corresponds to any of the aptamers listed in Table 3. In certain embodiment, the aptamer comprises any one of the aptamers listed in Table 3. In certain embodiment, the aptamer is a derivative of any one of the aptamers listed in Table 3, wherein the derivative is at least 90% identical in sequence to at least one aptamer listed in Table 3. In certain embodiment, the aptamer is a derivative of any one of the aptamers listed in Table 3, wherein the derivative is at least 95% identical in sequence to at least one aptamer listed in Table 3. In certain embodiment, the aptamer is a functional fragment of any one of the aptamers listed in Table 3.

TABLE 3

Fluorescent aptamer-fluorophore combinations.

| Fluorophore | Aptamer SEQ ID NO: | Ext. Max (nm) | Ems. Max (nm) | Extinction coefficient ($M^{-1}cm^{-1}$) | Fluorescence quantum yield | $K_D$ (nM) | Brightness |
|---|---|---|---|---|---|---|---|
| Spinach2-DHFBI | 2 | 423 | 489 | 22,000 | 0.72 | 530 | 100 |
| Spinach2-DHFBI-1T | 2 | 482 | 505 | 31,000 | 0.94 | 560 | 184 |
| Spinach2-DHFBI-2T | 2 | 500 | 523 | 29,000 | 0.12 | 1300 | 22 |
| Brocolli-DHFBI-1T | 3 | 472 | 507 | 29,600 | 0.94 | 360 | 96 |
| Mango-TO1-Biotin | 4 | 510 | 535 | 77,500 | 0.14 | 3.2 | Not available |

The term "a functional fragment" as used herein refers to any fragment of the original sequence which maintains at least 1% of the activity of the original sequence. In some embodiments, the functional fragment maintains at least 10% of the activity of the original sequence. In some embodiments, the functional fragment maintains at least 30% of the activity of the original sequence. In some embodiments, the functional fragment maintains at least 50% of the activity of the original sequence. In some embodiments, the functional fragment maintains at least 70% of the activity of the original sequence. In some embodiments, the functional fragment maintains at least 90% of the activity of the original sequence.

The term "functional homolog" as used herein refers to any sequence having at least 80% identity to the original sequence, which maintains at least 10% of the activity of the original sequence. In some embodiments, the functional homolog has at least 90% identity to the original sequence. In some embodiments, the functional homolog has at least 95% identity to the original sequence. In some embodiments, the functional homolog maintains at least 30% of the activity of the original sequence. In some embodiments, the functional homolog maintains at least 70% of the activity of the original sequence. In some embodiments, the functional homolog maintains at least 70% of the activity of the original sequence. In some embodiments, the functional homolog maintains at least 90% of the activity of the original sequence. In some embodiments, the functional In some embodiments, the tRNA molecule comprises at least two different signal-emitting aptamers. In some embodiments, each one of the at least two different signal-emitting aptamers emits a different signal. In some embodiments, each one of the at least two different signal-emitting aptamers binds a different ligand.

In some embodiments, the signal-emitting ligand is hydroxy benzylideneimidazolinone (HBI), a derivative of HBI, thiazole orange (TO), or a derivative of TO. In some embodiments, the signal-emitting ligand is 3,5-difluoro-4-hydroxy benzylideneimidazolinone (DFHBI), DFHBI-1T, DFHBI-2T or TO1-Biotin. Each possibility represents a separate embodiment of the invention.

In some embodiments, the tRNA molecule further comprises a CCA tail. The term "CCA tail" as used herein refers to ACCA (SEQ ID NO: 7) or UCCA (SEQ ID NO: 8) or GCCA (SEQ ID NO: 9) or CCA 3'-terminal group linked to the acceptor stem used to attach an amino acid to the tRNA molecule. The CCA tail is a cytosine-cytosine-adenine sequence at the 3' end of the tRNA molecule. The amino acid loaded onto the tRNA by aminoacyl tRNA synthetases, to form aminoacyl-tRNA, is covalently bonded to the 3'-hydroxyl group on the CCA tail. This sequence is important for the recognition of tRNA by enzymes and critical in translation. In prokaryotes, the CCA sequence is transcribed in some tRNA sequences. In most prokaryotic tRNAs and eukaryotic tRNAs, the CCA sequence is added during processing and therefore does not appear in the tRNA gene.

In some embodiments, the tRNA molecule of the present invention further comprises an amino acid. In some embodiments, the tRNA molecule is derived from a eukaryotic tRNA molecule. In some embodiments, the tRNA molecule is derived from a prokaryotic tRNA molecule.

The phrase "derived from a eukaryotic tRNA molecule" as used herein means that the pre-aptamer and post-aptamer sequences of a recombinant tRNA molecule are at least 90%, at least 95 or 100% identical to sequences of matching length found in a natural tRNA molecule of a eukaryotic organism.

The phrase "derived from a prokaryotic tRNA molecule" as used herein means that the pre-aptamer and post-aptamer sequences of the recombinant tRNA molecule are at least 90%, at least 95% or 100% identical to sequences of matching length found in a natural tRNA molecule of a prokaryotic organism.

The terms "pre-aptamer" and "post-aptamer" as used herein refer to RNA sequences of a recombinant tRNA located 5' and 3' to the aptamer sequence.

The term "at least 90% identical to sequences of matching length" as used herein refers to a sequence which is up to 10% longer, up to 10% shorter and/or different in up to 10% of its ribonucleotides compared to a sequence of matching length.

In some embodiments, the tRNA molecule described above is bound to a ligand. In some embodiments, the ligand is a signal-emitting ligand.

The present invention further provides, in another aspect, an oligonucleotide construct, comprising the sequence of any one of the recombinant tRNA molecules described above, or a complementary sequence thereof.

The present invention further provides, in another aspect, an expression vector, comprising a DNA oligonucleotide sequence encoding any one of the recombinant tRNA molecules described above; and a promoter operatively linked to the DNA oligonucleotide sequence.

The term "promoter" as used herein refers to a region of DNA upstream from the transcription start that is typically involved in binding RNA polymerase and other proteins in order to initiate transcription. Reference herein to a "promoter" is to be taken in its broadest context and includes the transcriptional regulatory sequences derived from a classical eukaryotic genomic gene, including the TATA (SEQ ID NO: 10) box which is required for accurate transcription initiation, with or without a CCAAT (SEQ ID NO: 11) box sequence and additional regulatory elements (i.e. upstream activating sequences, enhancers and silencers) which alter gene expression in response to developmental and/or external stimuli, or in a tissue-specific manner. Consequently, a repressible promoter's rate of transcription decreases in response to a repressing agent. An inducible promoter's rate of transcription increases in response to an inducing agent. A constitutive promoter's rate of transcription is not specifically regulated, though it can vary under the influence of general metabolic conditions. The term "promoter" also includes the transcriptional regulatory sequences of a classical prokaryotic gene, in which case it may include a −35 box sequence and/or a −10 box transcriptional regulatory sequences. The term "promoter" is also used to describe a synthetic or fusion molecule, or derivative which confers, activates or enhances expression of a nucleic acid molecule in a cell, tissue or organ. In some embodiments, the promoter is capable of being transcribed by a RNA polymerase I, RNA polymerase II, RNA polymerase III, RNA polymerase IV and/or RNA polymerase V. In some embodiments, the promoter is capable of being transcribed by a RNA polymerase III. In some embodiments, the promoter is capable of being transcribed by a RNA polymerase III only.

The term "operatively linked" as used herein refers to the ability of the promotor to directly or indirectly promote transcription of the DNA oligonucleotide sequence into an RNA oligonucleotide molecule.

In some embodiments, the promoter is a constitutive promoter. In some embodiments, the promoter is an inducible promoter. In some embodiments, the promoter is a eukaryotic promoter. In some embodiments, the promoter is a prokaryotic promoter. In some embodiments, the promoter is a constitutive eukaryotic promoter. In some embodiments, the promoter is an inducible eukaryotic promoter. In some embodiments, the promoter is a constitutive prokaryotic promoter. In some embodiments, the promoter is an inducible prokaryotic promoter.

The term "constitutive promotor" as used herein refers to a promotor which is substantially constitutively active in the cell. Non-limiting examples of constitutive promotors are the promotors driving expression of so-called "house-keeping" genes, which are responsible to an elevated, constant level of expression.

The term "inducible promotor" as used herein refers to a promotor which needs to be triggered to be active in the cell. Non-limiting examples of inducible promotors are the promotors driving expression of so-called "heat-shock" genes, which are responsible to an acute rise in the level of expression of certain proteins upon exposure of the cell to extreme temperatures. More non-limiting examples of inducible promotors are those requiring an external signal to the cell to become active, such as exposure to IPTG or DFHBI, as exemplified herein.

The terms "eukaryotic promoter" or "prokaryotic promotor" as used herein refer to promotors recognized by the transcription machinery of a eukaryotic or a prokaryotic cell, respectively.

In some embodiments, the expression vector further comprises a polynucleotide sequence encoding at least one component selected from the group consisting of a negative regulatory control element, a positive regulatory control element, a transcriptional terminator, and a selection marker gene.

The term "negative regulatory control element" as used herein refers to a region of DNA which encodes for a peptide or a protein having a negative effect on the transcription level of the DNA sequence encoding the tRNA molecules provided by the present invention. Non-limiting examples for negative regulatory control elements are peptides or proteins which physically bind to a promotor and eliminate transcription from said promotor. Such negative effect on transcription level can be alleviated, for example, by lowering the level of the promotor-binding peptides or proteins, and/or by binding said peptides or proteins by a molecule that prevents or weakens their binding to the promotor.

The term "positive regulatory control element" as used herein refers to a region of DNA which encodes for a peptide or a protein having a positive effect on the transcription level of the DNA sequence encoding the tRNA molecules provided by the present invention. Non-limiting examples for negative regulatory control elements are transcription enhancers, which are short (50-1500 bp) regions of DNA that can be bound with peptides or proteins (activators) to activate transcription of a gene or transcription. These peptides or proteins are usually referred to as transcription factors. Enhancers are generally cis-acting, located up to 1 Mbp (1,000,000 bp) away from the gene and can be upstream or downstream from the start site, and either in the forward or backward direction. There are hundreds of thousands of enhancers in the human genome.

The term "transcriptional terminator" as used herein refers to a section of nucleic acid sequence that marks the end of a gene or operon in genomic DNA during transcription. This sequence mediates transcriptional termination by providing signals in the newly synthesized RNA that trigger processes which release the RNA from the transcriptional complex. These processes include the direct interaction of the RNA secondary structure with the complex and/or the indirect activities of recruited termination factors. Release of the transcriptional complex frees RNA polymerase and related transcriptional machinery to begin transcription of new RNAs.

The term "selection marker gene" as used herein refers to a gene introduced into a cell, especially a bacterium or to cells in culture, which confers a trait suitable for artificial selection. They are a type of reporter gene used in laboratory microbiology, molecular biology, and genetic engineering to indicate the success of a transfection or other procedure meant to introduce foreign DNA into a cell. Selectable markers are often antibiotic resistance genes; bacteria that have been subjected to a procedure to introduce foreign DNA are grown on a medium containing an antibiotic, and those bacterial colonies that can grow have successfully taken up and expressed the introduced genetic material. Normally the genes encoding resistance to antibiotics such as ampicillin, chloramphenicol, tetracycline or kanamycin, etc., are considered useful selectable markers for *E. coli*.

The present invention further provides, in an aspect, a cell, comprising any one of the recombinant tRNA molecules described above, the oligonucleotide construct described above, or the expression vector described above, wherein the eukaryotic cell is not a human cell or wherein the eukaryotic cell is a human cell ex-vivo, not within a human body.

In some embodiments, the cell is a eukaryotic cell is a human cell.

In some embodiments, the eukaryotic cell is a human cell.

In some embodiments, the eukaryotic cell is a human cell, not within a human body.

In some embodiments, the eukaryotic cell is a human cell, ex vivo.

In some embodiments, the cell comprises a recombinant tRNA molecule as disclosed herein. In some embodiments, the cell comprises a recombinant tRNA molecule comprising an acceptor stem, a D stem, an anticodon arm, a T stem, and at least one aptamer.

In some embodiments, the cell comprises the oligonucleotide construct described herein. In some embodiments, the cell comprises an oligonucleotide construct comprising the sequence of the recombinant tRNA molecule described herein, or a complementary sequence thereof.

In some embodiments, the cell comprises the expression vector described herein. In some embodiments, the cell comprises an expression vector comprising:
i. a DNA oligonucleotide sequence encoding the recombinant tRNA molecule disclosed herein; and
ii. a promoter operatively linked to the DNA oligonucleotide sequence.

The present invention further provides, in another aspect, a prokaryotic cell, comprising any one of the recombinant tRNA molecules described above, the oligonucleotide construct of described above, or the expression vector described above.

In some embodiments, the prokaryotic cell is an *E. Coli* cell.

In some embodiments, the cell described above is a transgenic cell. In some embodiments, the transgenic cell is derived from a transgenic organism.

The present invention further provides, in another aspect, a method of monitoring a recombinant tRNA molecule, comprising the steps of (i) obtaining a recombinant tRNA molecule as described above; (ii) optionally, contacting the recombinant tRNA molecule with a ligand capable of binding the aptamer of the tRNA molecule; and (iii) monitoring the signal emitted by the aptamer of the recombinant tRNA molecule.

In some embodiments, the method comprising the steps of (i) obtaining a recombinant tRNA molecule as described above; and (ii) monitoring the signal emitted by the aptamer of the recombinant tRNA molecule. In some embodiment, the method further comprises the step of contacting the recombinant tRNA molecule with a ligand capable of binding the aptamer of the tRNA molecule, prior to said monitoring. In some embodiments, the method further comprises the steps of: contacting the recombinant tRNA molecule of the previous steps with a signal-emitting ligand capable of being bound by the aptamer of the tRNA molecule; and monitoring the signal emitted by the signal-emitting ligand; thereby monitoring the recombinant RNA.

The present invention further provides, in another aspect, a method of monitoring a recombinant tRNA molecule, comprising the steps of obtaining a recombinant tRNA molecule described above, or an expression vector described above; optionally, inducing expression of the recombinant tRNA molecule from the expression vector of the previous step; contacting the recombinant tRNA molecule of the previous steps with a signal-emitting ligand capable of being bound by the aptamer of the tRNA molecule; and monitoring the signal emitted by the signal-emitting ligand; thereby monitoring the recombinant RNA.

The term "monitoring" as used herein includes, but is not limited to, watching, detecting, analyzing, and/or accumulating, once or in a plurality of occasions, signals emitted by the recombinant tRNA molecule. The term "monitoring a tRNA molecule" as used herein includes, but is not limited to, detecting the presence of a tRNA molecule and/or monitoring activities associated with tRNA, such as, transcription, translation, protein synthesis, level (amount) of tRNA, nucleoli localization within a cell, rate of translation and quality of translation, diffusion rates (e.g. by fluctuation analysis) and others.

In some embodiments, the method further comprises the step of inducing the expression of the recombinant tRNA molecule from the expression vector. In some embodiments, the method further comprises monitoring an interaction between the recombinant tRNA molecule and an additional molecule. In some embodiments, the method further comprises monitoring ribosomal activity. In some embodiments, the method further comprises monitoring mRNA translation. In some embodiments, the method further comprises monitoring protein synthesis. In some embodiments, the method further comprises monitoring a stress response in a cell, tissue or organ. In some embodiments, the method further comprises monitoring the level of tRNA. In some embodiments, the method further comprises monitoring nucleoli localization in a cell. In some embodiments, the method further comprises monitoring tRNA transport and localization within the cell.

The term "stress" as used herein refers to any significant deviation from normal physiological conditions in a cell. No-limiting examples of internal causes of cellular stress are starvation, nutrient deficiency and oxygen deficiency. Non-limiting examples of external causes of cellular stress are extreme temperatures, exposure to radiation and dryness.

The terms "stress response" and "response to stress" as used herein are interchangeable and refer to a physiological response in a biological sample (e.g., a cell) to a stressful stimulus. No-limiting examples of stressful stimuli are provided above and further include toxins (e.g., chemotherapeutic agents, heavy metals, toxic chemicals, etc.), irradiation, extreme heat or cold, hypoxia, mechanical stress, shortage of nutrients, and/or endoplasmic reticulum (ER) stress.

In some embodiments, the method further comprises monitoring a tRNA-related disease. In some embodiments, the tRNA-related disease is associated with mutations in tRNA genes. In some embodiments, the tRNA-related disease is selected from the group consisting of combined oxidative phosphorylation defect (COXPD); mitochondrial encephalomyopathy, lactic acidosis and stroke-like episodes (MELAS); myoclonic epilepsy with ragged-red fibres (MERRF); cardiomyopathy; chronic ophthalmoplegia; ragged-red fibres (RRFs); cataract, spastic paraparesis and ataxia; neonatal death; ataxia; myopathy; leigh syndrome; and hypertension. In some embodiments, the RNA-related disease is associated with mutations in tRNA processing, charging and modification enzymes. In some embodiments, the tRNA-related disease is selected from the group consisting of type 2 diabetes mellitus; cancer; myopathy, lactic acidosis and sideroblastic anaemia (MLASA); Leukoencephalopathy with brain stem and spinal cord involvement and lactate elevation (LBSL); recessive ataxia; myopathy and infantile Charcot-Marie-Tooth; intellectual disability; dubowitz syndrome; Charcot-Marie-Tooth syndrome; dominant intermediate Charcot-Marie-Tooth syndrome; pontocerebellar hypoplasia; and perrault syndrome. In some embodiments, the tRNA-related disease is associated with alterations in the tRNA pool. In some embodiments, the tRNA-related disease is selected from the group consisting of type 2 diabetes mellitus; cancer; Huntington disease; influenza infection; vaccinia infection; West Nile virus infection; Japanese encephalitis virus infection; and human immunodeficiency virus (HIV) infection.

In some embodiments, the method is performed in a cell. In some embodiments, the cell is a eukaryote cell. In some embodiments, the cell is a prokaryote cell. In some embodiments, the method is carried out ex-vivo. In some embodiments, the expression vector comprises a constitutive promoter. In some embodiments, the expression vector comprises an inducible promoter, and the method further comprises the step of contacting the expression vector with a transcription-promoting ligand.

The present invention provides, in another aspect, a non-human organism, comprising any one of the recombinant tRNA molecules, the oligonucleotide constructs, or the expression vectors described above.

The present invention provides, in another aspect, a transgenic non-human organism, comprising a gene encoding any one of the recombinant tRNA molecules described above.

In some embodiments, the gene is a genomic or nuclear gene. In some embodiments, the gene is a mitochondrial gene.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" or "comprising," when used in this specification, specify the presence of stated features, integers, steps, operations, elements, or components, but do not preclude or rule out the presence or addition of one or more other features, integers, steps, operations, elements, components, or groups thereof.

While the present invention has been described with reference to some embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

EXAMPLES

The following examples are presented in order to more fully illustrate some embodiments of the invention. They should, in no way be construed, however, as limiting the broad scope of the invention.

Example 1. Design of Spinach tRNA

Figure 1B:
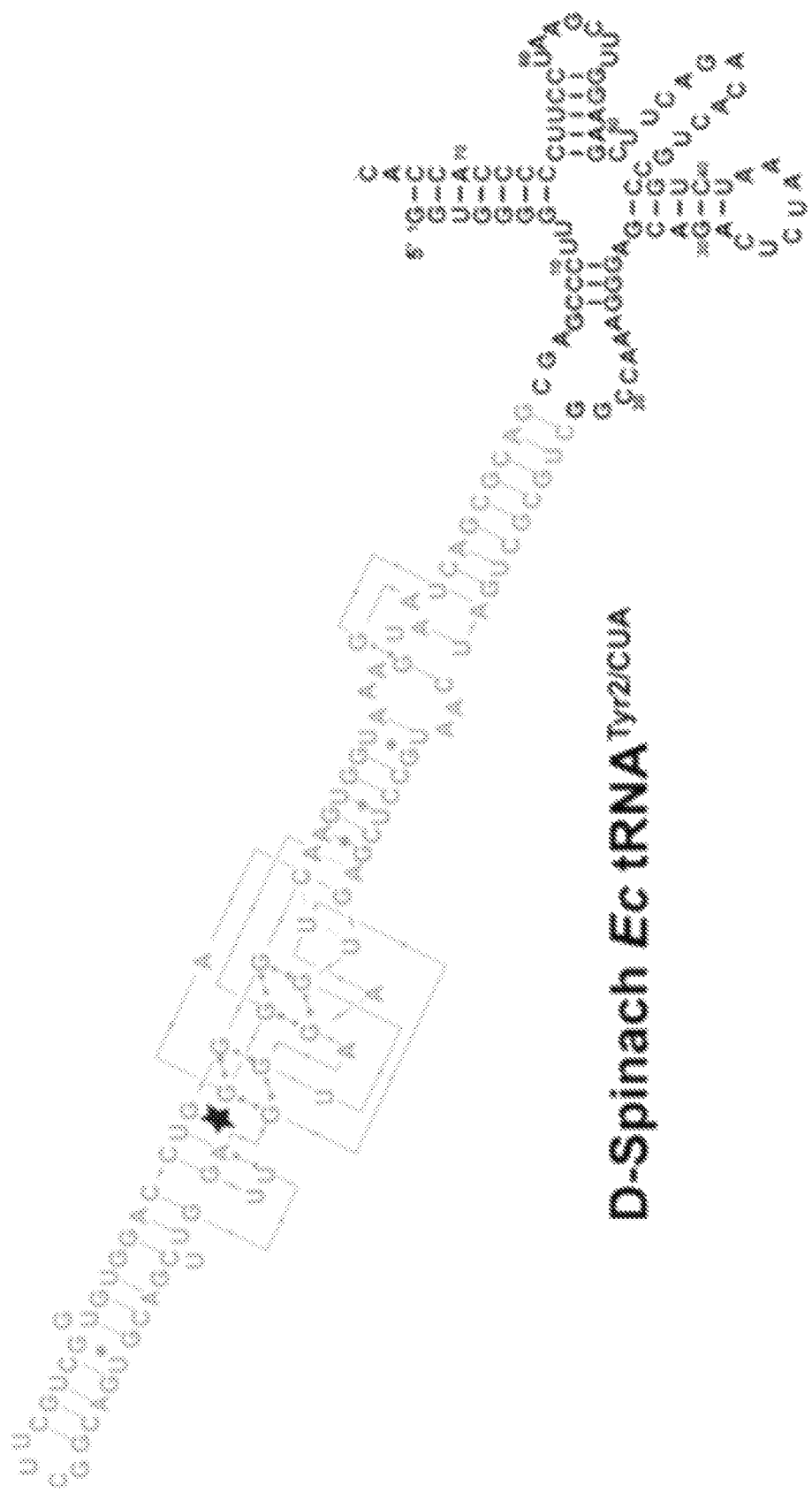
FIG. 1B exhibits sequence and secondary structure of Spinach to E.Coli tRNA$^{Tyr2}$ fusion in the D-loop (D-Spinach) (SEQ ID NO: 13), where the star indicates the bound ligand DFHBI.
Figure 1C:
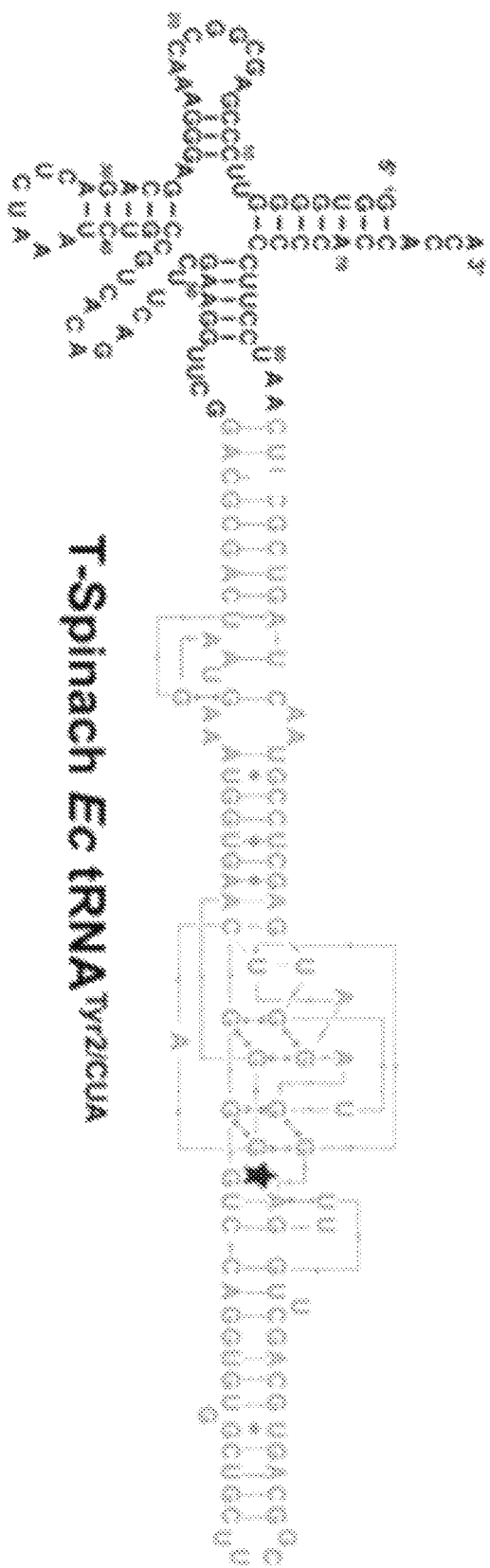
FIG. 1C exhibits sequence and secondary structure of Spinach to E. Coli tRNA$^{Tyr2}$ fusion in the T-loop (T-Spinach) (SEQ ID NO: 14), where the star indicates the bound ligand DFHBI.
Figure 1D:
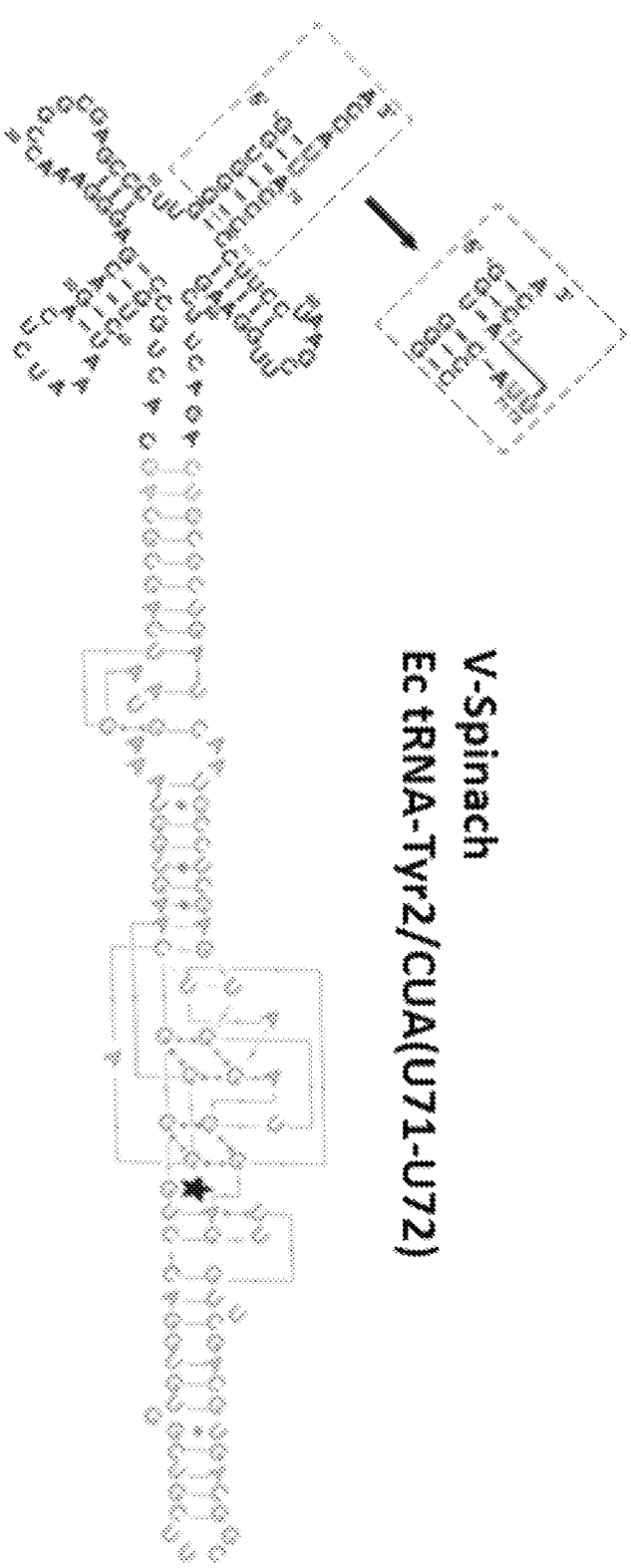
FIG. 1D exhibits sequence and secondary structure of Spinach to E.Coli tRNA$^{Tyr2}$ fusion in the V-loop with U71 and U72 substitutions in the acceptor stem, resulting in the G1-U72 and G2-U71 base pairs (V-Spinach U71-U72) (SEQ ID NO: 15), where the star indicates the bound ligand DFHBI.

*E. Coli* tRNA$^{Tyr2}$ (*E. Coli* tRNA$^{Tyr}$) was used as the framework to introduce the Spinach motif. *E. Coli* tRNA$^{Tyr2}$ differs from *E. Coli* tRNA$^{Tyr1}$ by only two nucleotides in the V-loop (C47:2 and A47:3 vs. U47:2 and C47:3) and is unlikely to differ from *E. Coli* tRNA$^{Tyr1}$ in charging specificity and activity in protein synthesis. tRNA$^{Tyr2}$ is referred to as tRNA$^{Tyr}$ in the Examples. While *E. Coli* tRNA$^{Tyr}$ has a standard T-loop, it has a large D- and V-loop, indicating the possibility to accommodate additional motifs in these two regions. Three chimeras of *E. Coli* tRNA$^{Tyr}$ were made, in which the Spinach motif was inserted to the V-loop between C47:2 and A47:3 (FIG. 1A; V-Spinach), to the D-loop between C16 and G18 (FIG. 1B; D-Spinach) and to the T loop between G57 and A58 (FIG. 1C; T-Spinach). The secondary structure of the Spinach motif as drawn in FIGS. 1A-1D based on crystal structures of the aptamer. Of these, only the V-Spinach fusion was stably expressed, indicating acceptance of the new motif by enzymes such as tyrosyl-tRNA synthetase (TyrRS). Indeed, a co-crystal structure of TyrRS-tRNA$^{Tyr}$ reveals that the large V loop is well accommodated by TyrRS using a C-terminal domain that stabilizes the unique shape of the loop. In bacteria, tRNA$^{Ser}$ and tRNA$^{Leu}$ also have a large V-loop and are attractive for making Spinach chimeras, whereas in mammalian cells, tRNA$^{Ser}$ and tRNA$^{Leu}$ are potential candidates but not tRNA$^{Tyr}$, which has instead a smaller V-loop.

Example 2. V-Spinach tRNA$^{Tyr/CUA}$

The Spinach aptamer adopts an elongated structure of two coaxially stacked helical stems, which are joined by a G-quadruplex motif that binds the ligand 3,5-difluoro-4-hydroxy benzylideneimidazolinone (DFHBI). The tRNA architecture features D, V, and T-loops, which form long-range interactions to fold the cloverleaf secondary structure into an L-shaped tertiary structure (e.g. FIG. 1A-1D). Notably, the U71-U72 variant in (FIG. 1D; V-Spinach (U71-U72)) has the potential to re-arrange the AU$^{71}$UACCA$^{76}$ (SEQ ID NO: 12) sequence such that the AU$^{71}$U$^{72}$ nucleotides are bulged out from the acceptor stem and the remaining nucleotides A$^{73}$CCA$^{76}$ (SEQ ID NO: 7) are paired to the acceptor stem. This alternative structure has been shown in E. Coli tRNA to be unstable.

To make a fusion construct, E. Coli tRNA$^{Tyr}$ was chosen as the framework, which has a naturally large D- and V-loop relative to the average, indicating a capacity of these regions to accommodate new structural motifs. The stable expression level of the V-Spinach fusion in E. Coli cells was similar in the tRNA native form with the natural anticodon 5'-GUA and in the amber suppressor form with the amber-reading anticodon 5'-CUA. This supports the notion that the V-loop is a suitable site for accepting the Spinach aptamer without compromising tRNA structural stability.

As exemplified below, in E. Coli cells, where a plasmid-borne V-Spinach tRNA$^{Tyr}$ was constitutively expressed, the GFP-like fluorescence was readily detected in virtually every single cell that was briefly incubated with DFHBI; in contrast, cells expressing Spinach alone showed no fluorescence, perhaps due to cellular instability of the aptamer. In cells where the expression was regulated by a transcriptional repressor, fluorescence of individual cells was dependent on induction of the fusion gene, showing a stable increase in intensity over time until well into the late-log phase of growth.

Figure 1E:
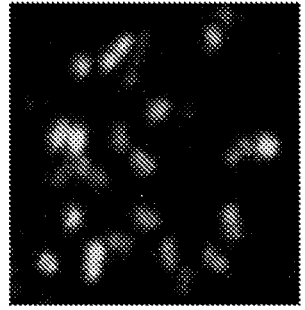
FIG. 1E exhibits fluorescence microscope images of E. Coli cells expressing the amber suppressor form of V-Spinach tRNA$^{Tyr}$ (top) and cells expressing the Spinach motif alone (bottom).
Figure 1E:
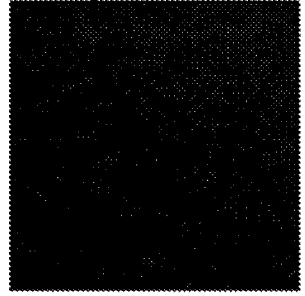
Figure 1F:
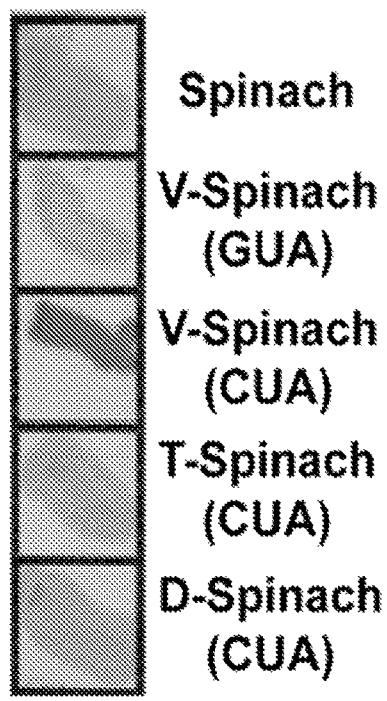
FIG. 1F exhibits suppression of the lacZ125am locus in E. Coli CA244 cells by V-Spinach tRNA$^{Tyr}$ with the 5'-CUA anticodon (CUA), but not by the Spinach motif alone, by V-Spinach tRNA$^{Tyr}$ with the 5'-GUA anticodon (GUA), or by T- or D-Spinach tRNA$^{Tyr}$ with the CUA anticodon (CUA).

As further exemplified below, to determine whether imaging of V-Spinach tRNA was associated with its protein synthesis activity or whether such a fusion tRNA was sterically excluded from the ribosomal machinery, E. Coli CA244 cells were used as the host, which harbor an amber codon (5'-UAG) mutation in the N-terminal half of β-galactosidase encoded by the lacZ125am gene. Full-length synthesis of β-galactosidase required suppression of the lacZ125am locus by a suppressor tRNA actively involved in live-cell protein synthesis. Surprisingly, it is shown that cellular expression of the amber-suppressor form of V-Spinach tRNA$^{Tyr}$, despite being in a large and bulky structure, readily suppressed the lacZ125am locus, as shown by synthesis of β-galactosidase on an X-gal indicator plate. This suppression demonstrated that V-Spinach tRNA$^{Tyr}$ was active in live-cell protein synthesis (FIGS. 1E and 1F). Suppression was only observed when the fusion tRNA had the amber-reading anticodon 5'-CUA; no suppression was observed in cells expressing the Spinach alone (FIG. 1F, top panel) or the amber suppressor form of T- or D-Spinach tRNA$^{Tyr}$ (FIG. 1F, bottom panels).

Example 3. Comparison Between Natural tRNA$^{Tyr}$ and V-Spinach tRNA$^{Tyr}$

Amber suppression indicates that V-Spinach tRNA$^{Tyr}$ was able to translate the amber codon in-vivo. Translation of a codon proceeds through at least five key steps; (i) aminoacylation of the tRNA cognate to the codon, (ii) formation of the aminoacyl-tRNA ternary complex with EF-Tu and GTP, (iii) ribosomal accommodation of the aminoacyl-tRNA upon recognition of the A-site codon, (iv) peptidyl transfer from the P- to the A-site tRNA on the ribosome, and (v) translocation of the ribosome complex to the next codon.

Figure 2A:
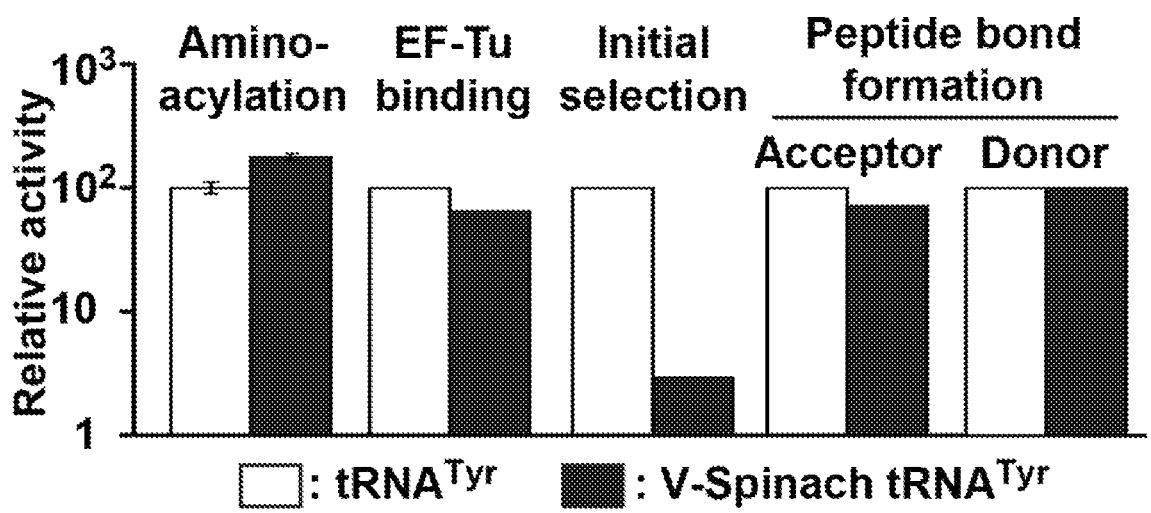
FIG. 2A exhibits relative activity of V-Spinach tRNA$^{Tyr}$ (black columns) versus E. Coli tRNA$^{Tyr}$ (white columns) in major steps of protein synthesis.

To gain insight into how the structurally bulky V-Spinach tRNA$^{Tyr}$ performed these reaction steps relative to the parental tRNA$^{Tyr}$, individual in-vitro steps were monitored using quantitative assays with purified enzymes and ribosomes. Each tRNA was expressed from a plasmid and was purified from E. Coli cells in the native form, with the 5'-GUA anticodon and all natural post-transcriptional modifications, so that data of quantitative assays would be relevant to tRNA biology in cells. Unexpectedly, it was found that V-Spinach tRNA$^{Tyr}$ was as active as tRNA$^{Tyr}$ in all reaction steps but step (iii): the initial selection for the anticodon-codon pairing interaction on the ribosome A-site (FIG. 2A).

Of the five reactions, aminoacylation (step (i)) and formation of an aminoacyl-tRNA ternary complex (step (ii)) were independent of the ribosome. Aminoacylation was catalyzed by tyrosyl-tRNA synthetase with Tyr, showing that V-Spinach tRNA$^{Tyr}$ and its parental tRNA$^{Tyr}$ exhibited similar catalytic turnover (kcat=0.9±0.1 vs. 1.2±0.1 s-1) and catalytic efficiency (kcat/Km=1.6±0.1 vs. 0.9±0.1 μM-1 s-1) with values well within the range of kinetic parameters of other E. Coli tRNAs. The high catalytic turnover and efficiency of V-Spinach tRNA$^{Tyr}$ indicates specificity of Tyr charging. The charged Tyr-tRNA must be stably captured in a ternary complex with EF-Tu and GTP for arrival at the ribosome. Measurement of dissociation from the respective ternary complexes in equilibrium conditions showed that the off rate of V-Spinach tRNA$^{Tyr}$ and of the parental tRNA$^{Tyr}$ was similar (koff=0.0034±0.0008 vs. 0.0022±0.0005 s-1), indicating comparable stability of their ternary complexes (Kd=31±1 vs. 20±1 nM).

After formation of each ternary complex, the next three steps (iii)-(v) were ribosome-dependent. Intriguingly, upon binding of each ternary complex to the A-site of a ribosome initiation complex, analysis of the EF-Tu-dependent GTP hydrolysis (step (iii)) showed that V-Spinach tRNA$^{Tyr}$ was at a 34-fold slower rate relative to tRNA$^{Tyr}$ (0.029±0.02 vs. 0.99±0.06 s-1). Despite this defect, assays for the next two rounds of peptidyl transfer showed little difference between the two. For example, in assays that monitored the first peptide bond formation (step (vi)), starting with V-Spinach tRNA$^{Tyr}$ reading the A-site codon to acting as the acceptor of the first peptidyl transfer, it was found that it was 48-fold slower relative to tRNA$^{Tyr}$ ($k_{obs}$=0.031±0.004 vs. 1.5±0.2 s-1). This is a rate reduction by only 1.4-fold considering that it was propagated from the rate reduction of GTP hydrolysis at the A-site (34-fold). Similarly, in assays that monitored two successive rounds of peptide bond formation (reaction v), starting with V-Spinach tRNA$^{Tyr}$ reading the A-site codon and ending with it acting as a donor for the second peptidyl transfer, it was found that it was 43-fold slower relative to tRNATyr ($k_{obs}$=0.0058±0.0004 vs. 0.25±0.04 s-1), a virtually identical rate reduction as that for the first peptidyl transfer. Because the ribosome must translocate from the Tyr to the next codon after synthesis of the first peptide bond, this result indicates that V-Spinach tRNA$^{Tyr}$ was functionally equivalent to its parental tRNA$^{Tyr}$ during translocation and formation of the second peptide bond.

Figure 2B:
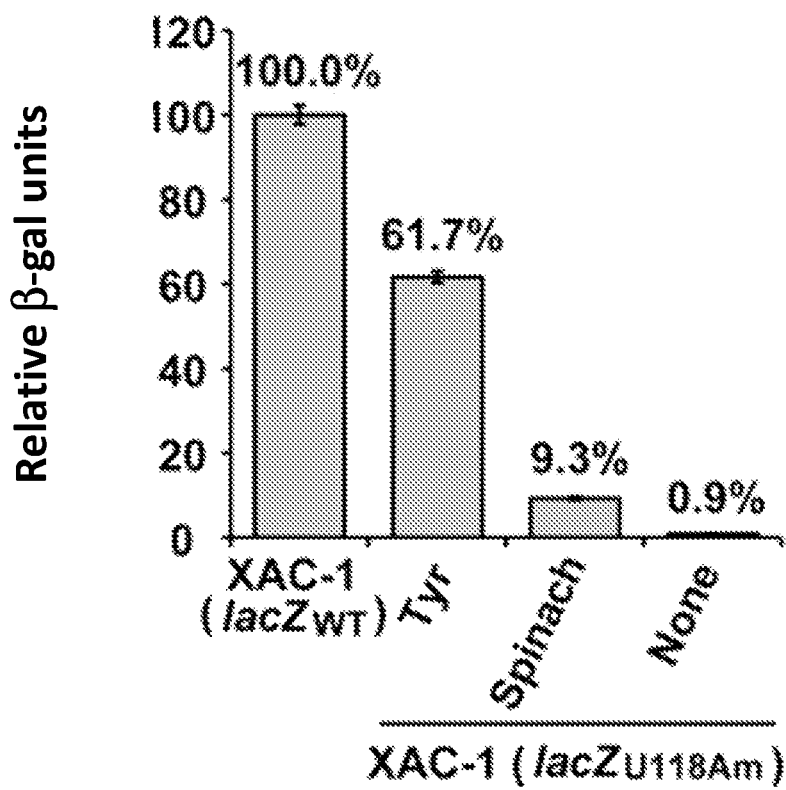
FIG. 2B exhibits suppression of the amber codon 5'-UAG at the lacZU$_{118Am}$ locus by the amber suppressor form of V-Spinach tRNA$_{Tyr}$ harboring the anticodon 5'-CUA, leading to synthesis of β-galactosidase, wherein each activity is reported as a fraction relative to the activity encoded by the lacZ$^{WT}$ gene (no amber mutation) in XAC-1 cells.
Figure 2C:
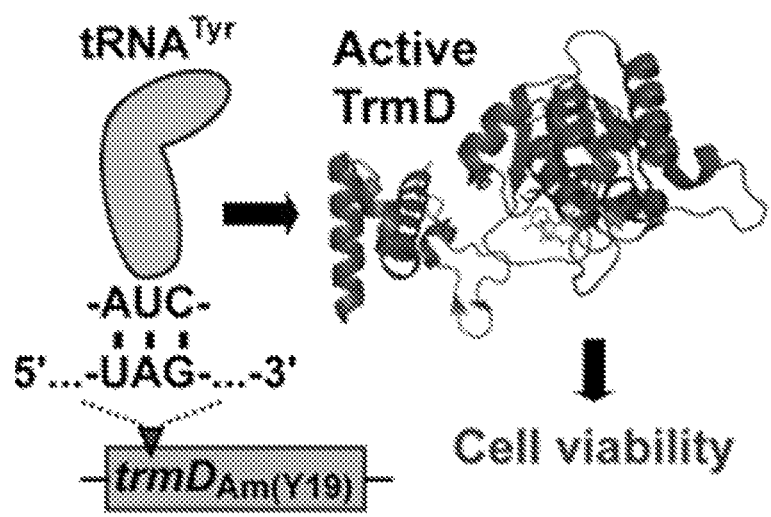
FIG. 2C exhibits the mechanism of trmDA$_{Am(Y19)}$ suppression by the amber suppressor form of V-Spinach tRNA$^{Tyr}$.

Knowing that V-Spinach tRNA$^{Tyr}$ was active in protein synthesis both in-vivo and in-vitro, its ability to maintain cell viability was determined. The mechanism of trmD$_{Am(Y19)}$ suppression by the amber suppressor form of V-Spinach tRNA$^{Tyr}$ is described in FIG. 2C. This process leads to synthesis of the growth-essential TrmD enzyme, that supports E. Coli cell viability. The trmD$_{Am(Y19)}$ locus contains an amber codon at the Tyr19 position, which prevents translation of the trmD gene. The study was conducted in E. Coli trmD-knockout (trmD-KO) cells where the chromosome-encoded trmD gene was disrupted with an antibiotic marker and cells were maintained viable in the presence of arabinose by a plasmid-borne and arabinose-controlled expression of the human counterpart gene trm5. The amber suppressor form of the tRNA was used to determine its suppression activity in E. Coli cells expressing a reporter lacZ$_{U118Am}$ gene, where an amber mutation was localized to position 17 of β-galactosidase. Measurement of β-galactosidase activity encoded in XAC-1 cells expressing a plasmid-borne amber suppressor form of tRNA$^{Tyr}$ (Tyr), amber suppressor form of V-Spinach tRNA$^{Tyr}$ (Spinach), or none were performed. The reporter activity in cells showed that translation at the amber codon by V-Spinach tRNA$^{Tyr}$ was 9.3% relative to the control gene without the amber mutation (lacZ$_{WT}$); this efficiency was lower compared to 61.7% of the parental tRNA$^{Tyr}$ in the amber suppressor form (FIG. 2B). Thus, consistent with reduced activities in protein synthesis in-vitro, the cellular protein synthesis activity of V-Spinach tRNA$^{Tyr}$ is reduced.

Figure 2D:
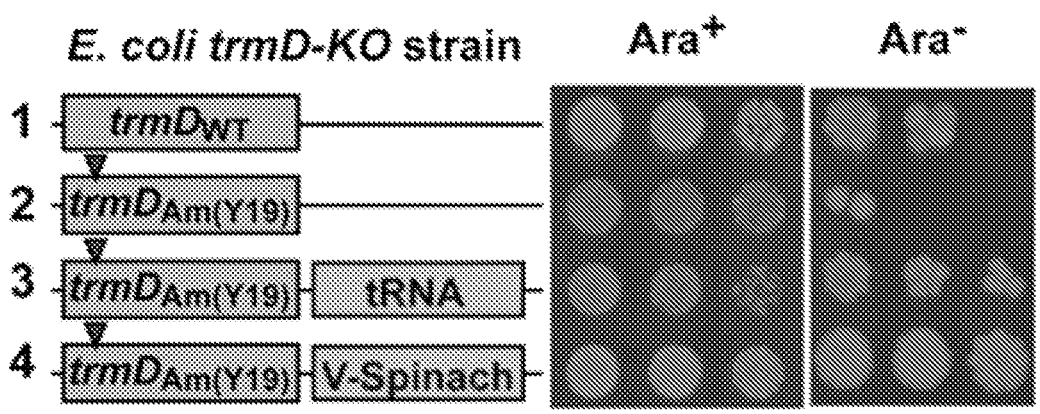
FIG. 2D exhibits examination of viability of E. Coli trmD-KO cells expressing a plasmid-borne trmD$_{WT}$ gene (row 1), a plasmid-borne trmDA$_{AM(Y19)}$ gene (row 2), a plasmid-borne trmDA$_{Am(Y19)}$ gene and the amber suppressor gene of E. ColiColi tRNA$^{Tyr}$ (row 3), and a plasmid-borne trmDA$_{Am(Y19)}$ gene and the amber suppressor gene of V-Spinach tRNA$^{Tyr}$ (row 4) in the presence or absence of arabinose (Ara). Error bars denote SD (standard deviation).

To determine if the reduction described above affected cell viability, the growth-essential trmD gene was chosen as a reporter, which codes for the tRNA methyl transferase for post-transcriptional methylation of G37 to m$^1$G37 on the 3' side of the anticodon. *E. Coli* cells harboring an amber mutation of the Tyr codon at position 19 of trmD were non-viable, unless the human counterpart gene encoded in a maintenance plasmid was turned on by addition of arabinose (FIG. 2D, rows 1-2). It was then shown that suppression of the amber mutation by the suppressor form of the parental tRNA$^{Tyr}$ was sufficiently active, such that cells were viable even when the human gene was turned off by removal of arabinose from growth media (FIG. 2D, row 3). Importantly, the suppressor form of V-Spinach tRNA$^{Tyr}$ was as active as the suppressor form of tRNA$^{Tyr}$, maintaining cell viability in the absence of arabinose (FIG. 2D, row 4). The data show that the live-cell protein synthesis activity of V-Spinach tRNA$^{Tyr}$ was sufficient to support cell growth.

ampicillin. The overnight culture was inoculated into 3 mL fresh media (by a 100-fold dilution) and grown for 3-4 hours at 37° C. to OD$_{600}$ of 0.3-0.4. The CA244 cells were harvested, while the JM109 cells were split into two tubes and 1 mM IPTG was added to one. At each point after induction, the culture of each tube (1.5 mL) was harvested. Cells were re-suspended in 150 µL of M9 media, washed twice in M9, and plated on the PDL-treated glass slides for 20 min at 37° C. After removal of free cells by washes with M9, the plates were incubated with 200 µM DFHBI in M9 for 5 min at 37° C. This was followed by additional washes of cells in M9 to remove excess DFHBI before imaging analysis. Live fluorescence images were obtained with a PTM camera through a 63× oil objective lens mounted on a Carl Zeiss LSM (Laser Scanning Microscopy) 510 META confocal microscope and analyzed with Metamorph software. An argon ion 488 nm laser was used for excitation and a 505-550 nm band pass filter (Carl Zeiss) was used to select the fluorescent signal. For time course analysis of fluorescence intensity, images were acquired every 30 min with 1024×1024 pixel resolution. The intensity of individual *E. Coli* cells at each time point was calculated by Metamorph software and was shown as the average (N=100 each).

Imaging of tRNA in CA244 cells represented the average level of de novo synthesis and decay. Among the more than 1000 cells examined, a significant fluorescence signal above the background for V-Spinach tRNA$^{Tyr}$ was observed with a steady increase from time 0 up to 2 hours, indicating that

TABLE 4

Comparison of the activity of V-Spinach tRNA vs. native tRNA$^{Tyr}$ on the ribosome.

| | k$_{obs (s}$$^{-1}$)** | | | Inhibition of kinetics by Spinach | |
|---|---|---|---|---|---|
| Reaction* | native | Spinach | Ratio | step | Decrease*** |
| GTP hydrolysis | 0.99 ± 0.06 | 0.029 ± 0.002 | 34 | decoding GTPase activation | 34-fold |
| First peptide formation | 1.5 ± 0.2 | 0.031 ± 0.004 | 48 | accommodation dipeptide formation | 1.4-fold |
| Second peptide formation | 0.25 ± 0.04 | 0.0058 ± 0.0004 | 43 | translocation tripeptide formation | None |

*Single-turnover reactions starting with 70S initiation complex conducted in HiFi buffer A at 20° C.
**Errors denote SDs for both GTP hydrolysis and peptide bond formation, which are derived from fitting data to the equation y = y$_0$ + A(1 − e$^{-k_{obs}t}$), where y$_0$ is the y intercept, A is a scaling constant, k$_{app}$ (or k$_{obs}$) is the apparent (or observed) rate constant and t is time in second.
***The kinetics of fMYP formation strongly suggests that the presence of the Spinach insert does not alter the second round of peptidyl transferase activity.

Example 4. Live Cell Imaging of *E. Coli* Cells Expressing V-Spinach tRNA

A pKK223-3-borne V-Spinach tRNA was expressed in one of three *E. Coli* strains: CA244 (Hfr (PO1)lacZ56 trp-49 relA1 SpoT), Top10 (F-mcrA Δ(mrr-hsdRMS-mcrBC) Φ80lacZΔM15 ΔlacX74 recA1 araD139 Δ(ara leu) 7697 galU galK rpsL (StrR) endA1 nupG) (Invitrogen), and JM109 (F' traD36 proA+B+lacIq Δ(lacZ)M15/Δ(lac-proAB) glnV44 e14-gyrA96 recA1 relA1 endA1 thi hsdR17). Expression in CA244 and in Top10 was constitutive, due to the lack the lacIq repressor in these cells, whereas expression in JM109 was IPTG-inducible to switch off the lacIq repressor in cells. Expression in all three strains showed no visible toxicity.

Prior to imaging analysis, optical glass slides were freshly coated with poly-D-lysine (PDL) for 1 hour at room temperature and washed twice with M9 minimal media. An overnight culture of *E. Coli* cells expressing a Spinach tRNA were grown in LB medium at 37° C. supplemented with de-novo synthesis of the tRNA was dominant over decay within this time frame. In contrast, cells expressing the U71-U72 variant of V-Spinach tRNA$^{Tyr}$ showed no fluorescence, indicating that decay was dominant over de-novo synthesis. The U71-U72 variant was designed to introduce instability to the acceptor stem, which had been shown to result in rapid decay.

Figure 3A:
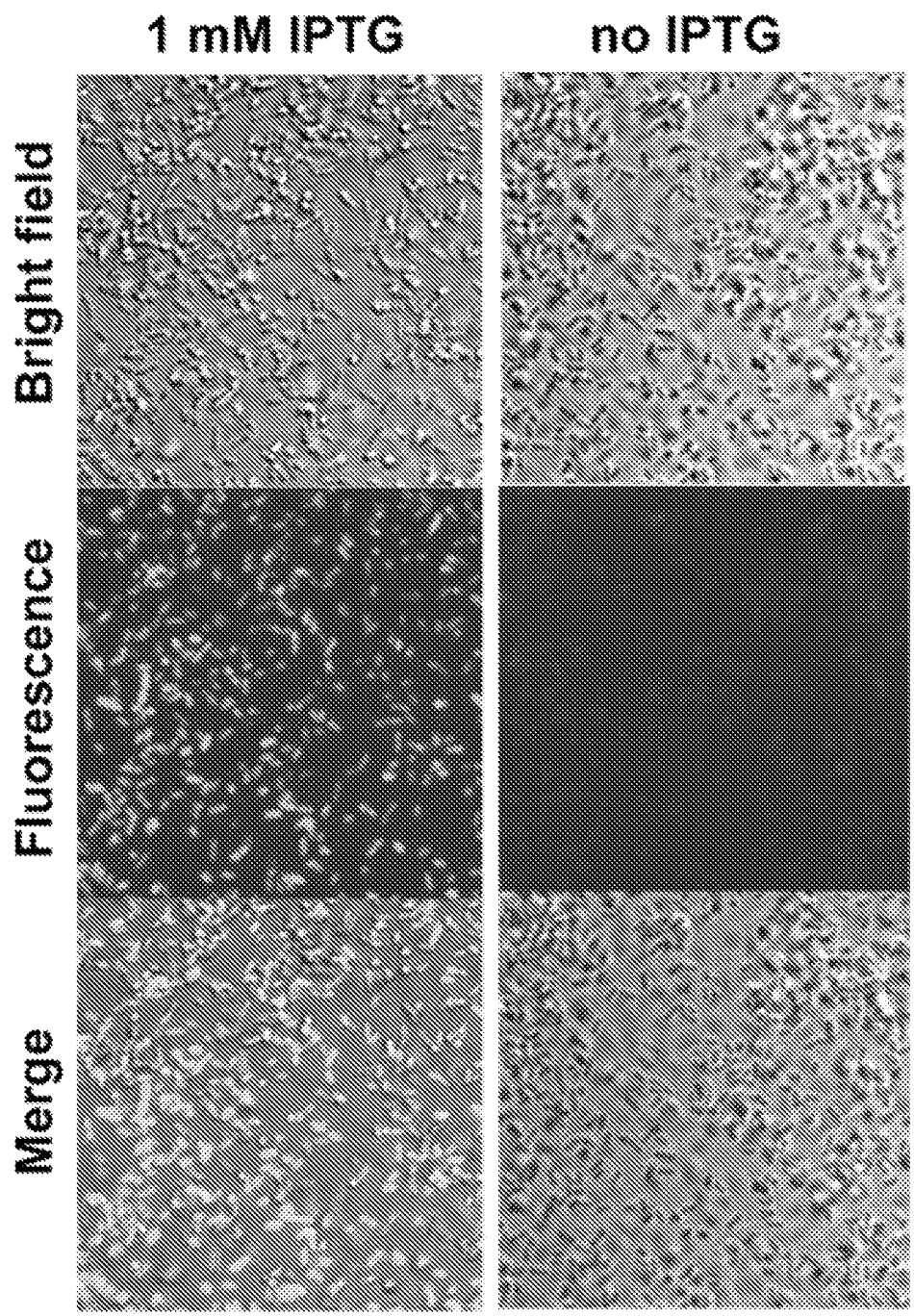
FIG. 3A exhibits fluorescence microscope image of E. Coli JM109 cells expressing V-Spinach tRNA$^{Tyr}$ upon 60-min induction with IPTG (left panels) relative to control cells (no-IPTG; right panels): in a bright field (top panels), fluorescence image excited by 488 nm Argon ion laser (middle panels), the merged image (bottom panels).
Figure 3B:
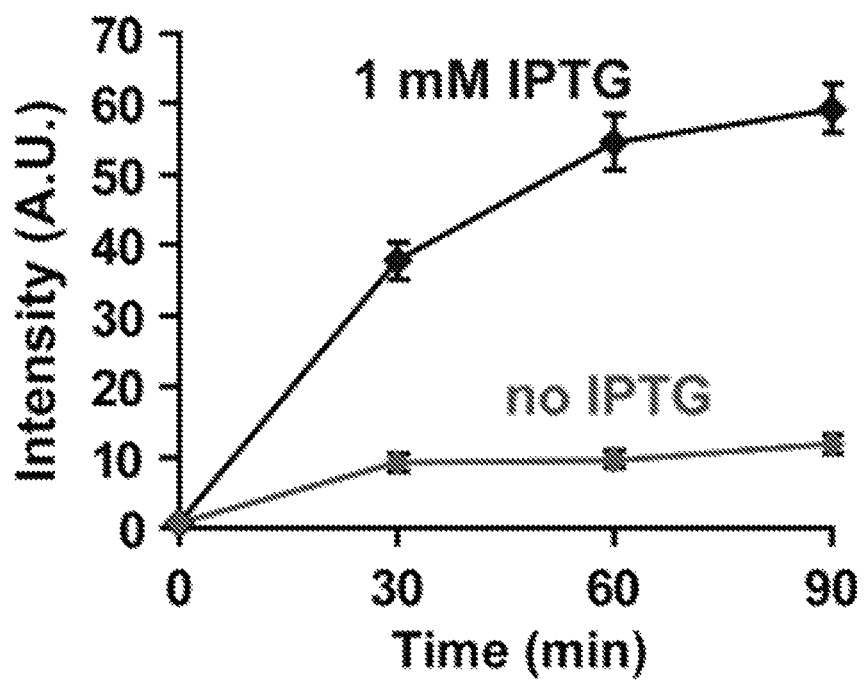
FIG. 3B exhibits quantification of fluorescence over the IPTG (1 mM)-induced time course (30, 60 and 90 min.) of E. Coli JM109 cells. Error bars are expressed as SEM, where N=100 for each of the time points.

JM109 cells expressing V-Spinach tRNATyr were imaged following induction with IPTG (FIG. 3A, left panels) relative to control cells (no-IPTG; FIG. 3B, right panels). Representative images at 60-min induction are shown in FIG. 3A. IPTG induction of Spinach-tRNA fusion was performed for 30, 60 or 90 min, and cells were washed and incubated with DFHBI on a slide glass for fluorescent imaging. Quantification, by an image analysis software, refers to average intensity of the pixels corresponding to the area of a single *E. Coli* cell (FIG. 3B). tRNA in JM109 cells showed a rapid increase in fluorescence upon IPTG induction, reaching a stable 60-fold increase over the baseline within 60 min, but a slow and small increase in fluorescence intensity in the absence of IPTG (FIG. 3B). The latter is attributed to the IPTG-independent basal expression from the pTac promoter. The results confirm that the fluorescence observed in E. Coli cells expressing V-Spinach tRNA$^{Tyr}$ was associated with the tRNA, rather than nonspecific effects on Spinach fluorescence.

Figure 4A:
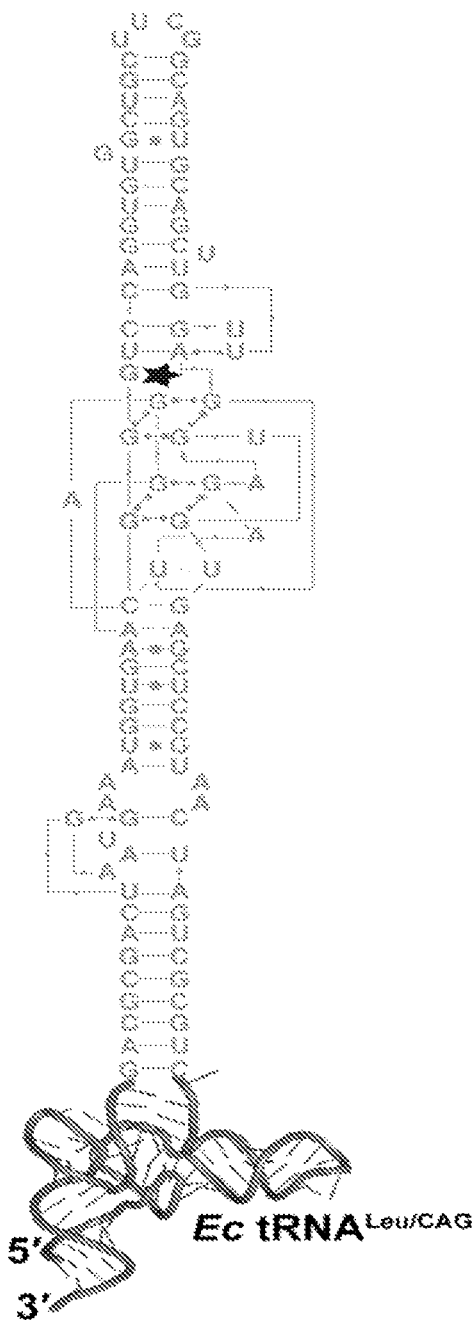
FIG. 4A is a schematic presentation of Spinach of SEQ ID NO: 1 inserted to the V-loop of E. Coli tRNA$^{Leu/CAG}$.
Figure 4B:
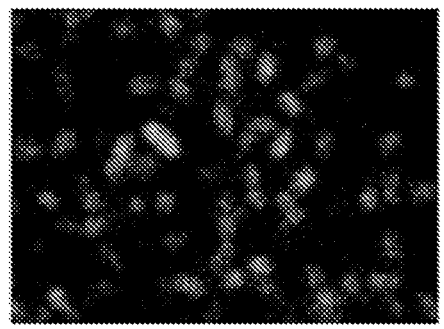
FIG. 4B exhibits fluorescence microscope image of E.Coli JM109 cells expressing V-Spinach tRNA$^{Leu/CAG}$ (upper panel), and fluorescence microscope image of E.Coli JM109 cells expressing tRNA$^{Leu/CAG}$, where the star indicates the bound ligand DFHBI.
Figure 4B:
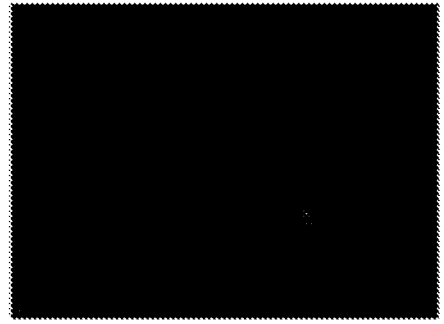

In summary, these experiments show that expression of V-Spinach tRNATyr is subject to promoter regulation. Importantly, live-cell fluorescence imaging was not specific to E. Coli tRNATyr, but was also applicable to a Spinach fusion to the V-loop of tRNALeu, another species in E. Coli with a large V-loop relative to the average (FIGS. 4A-4B). This indicates the potential to expand the live-cell imaging methodology of Spinach fusion to other tRNAs.

Example 5. Construction of Expression Vector for Use in Mammalian Cells

Figure 5A:
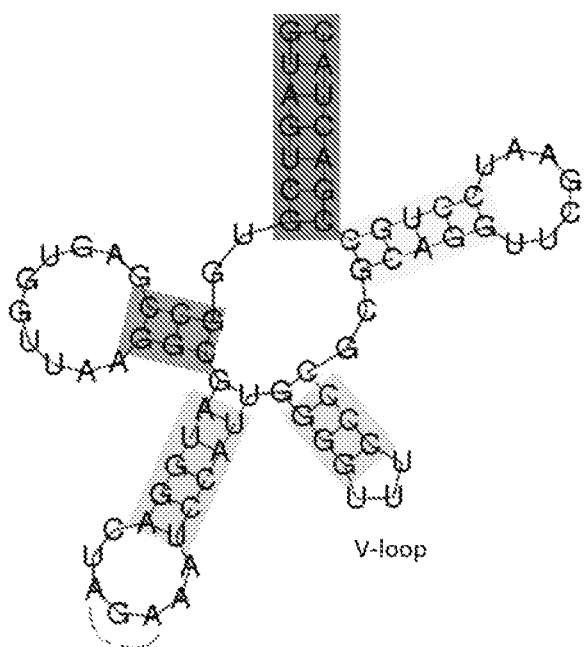
FIG. 5A is a schematic presentation of Broccoli inserted to the V-loop of tRNA$^{ser/AGA}$ (SEQ ID NO: 16).
Figure 5B:
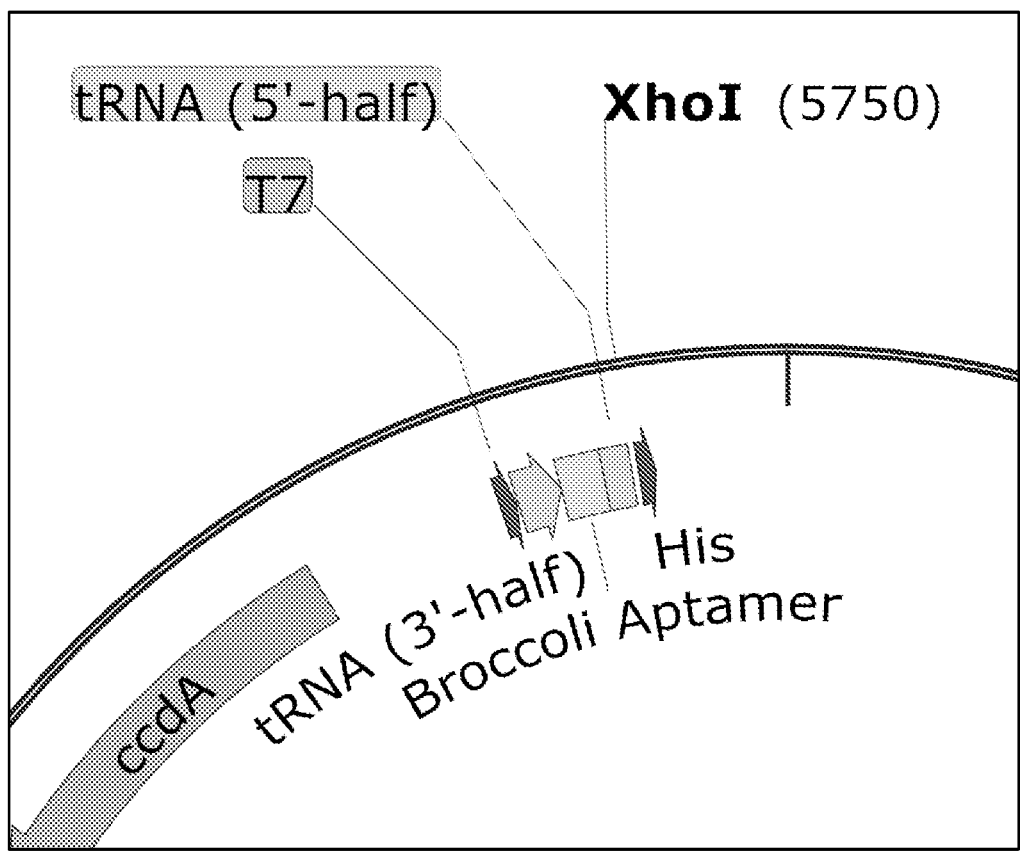
FIG. 5B is a schematic presentation of pStaby2.1-tRNA$^{ser}$ construct which includes the T7 promoter for in vitro transcription.
Figure 5C:
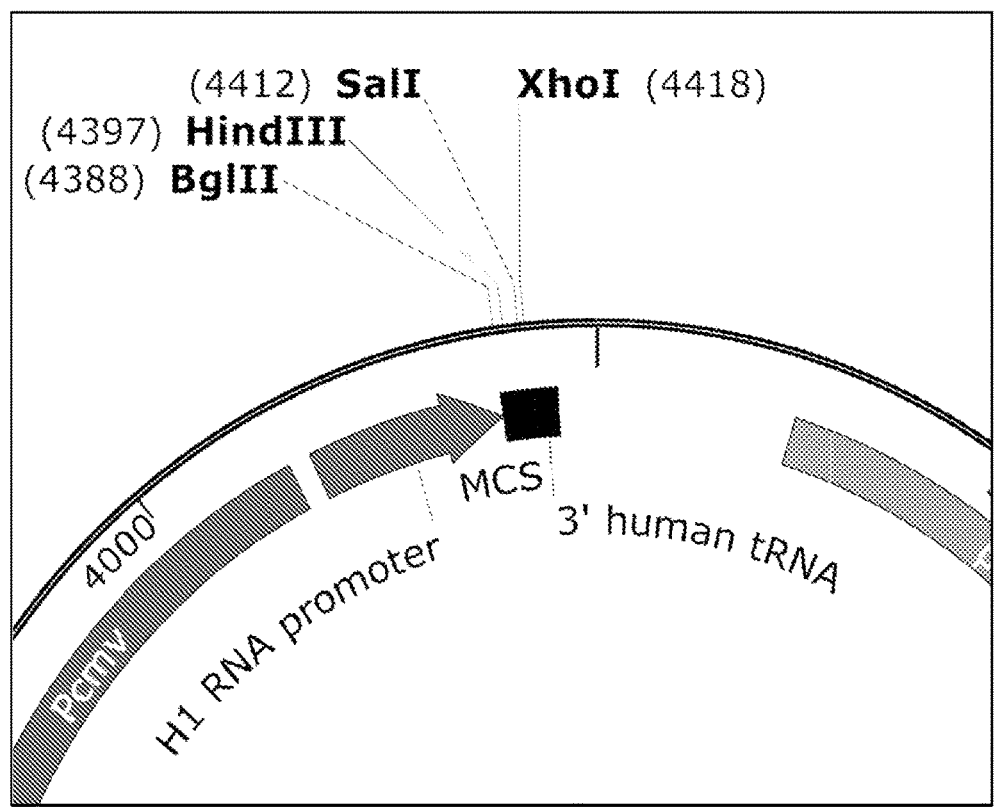
FIG. 5C is a schematic presentation of pStabyH1 prom-tRNA construct for mammalian expression, which includes the Histone 1 promoter for low level expression.

Broccoli is an RNA-based aptamer which binds to DFHBI and activates its green fluorescence. Two plasmids with a fusion of human tRNA$^{ser}$ to Broccoli Aptamer (SEQ ID NO: 3) were constructed, wherein the aptamer has been inserted in the V-loop of tRNA$^{ser/AGA}$ (FIG. 5A), as follows: (i) pStaby2.1-tRNAser, which includes the T7 promoter for in vitro transcription (FIG. 5B); and ii) pStabyH1prom-tRNA for mammalian expression, using the Histone 1 promoter for low level expression (FIG. 5C).

Figure 6:
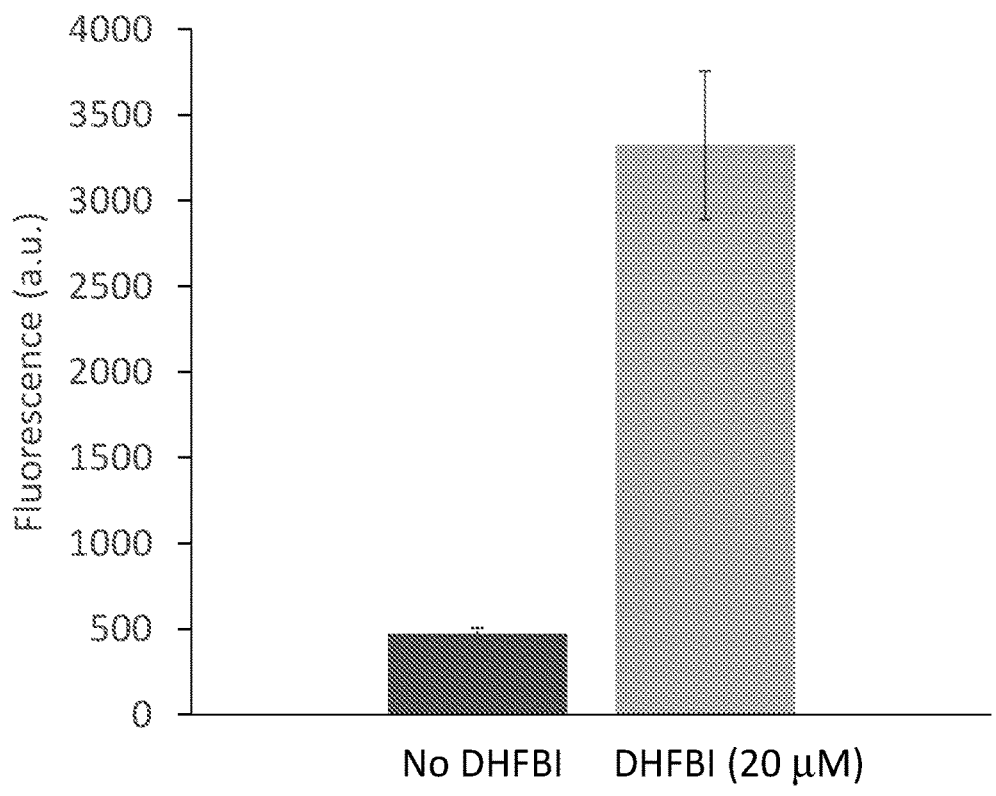
FIG. 6 exhibits fluorescent intensity in vitro of tRNA-aptamer construct in the absence or presence of DFHBI.

Example 6. In-Vitro Testing of Mammalian tRNA-Aptamers tRNAser-Aptamer was transcribed in vitro (MAXIscript T7 Kit, Ambion) and used in DFHBI fluorescent binding assay to demonstrate that the tRNA-aptamer construct is able to bind DFHBI and induce its fluorescence. In vitro transcribed tRNAser-Aptamer (2 µM) was heated to 70° C. for 10 minutes, magnesium chloride was added to a final concentration of 10 mM and the tRNA was slowly cooled to room temperature to enable correct folding. Subsequently, the folded tRNA (10 µl) was placed in 6 wells of a black, half-well, 96-well plate; to control wells (triplicates) an equal volume of fluorescent buffer (20 mM HEPES-KOH, pH 7.4, 100 mM KCl, 1 mM MgCl$_2$); to experimental wells (triplicates) an equal volume of fluorescent buffer containing 20 µM DFHBI were added. Fluorescent signal was measured at 25° C., at an excitation wavelength of 480 nm and emission wavelength of 505 nm and slit widths, 10 nm (Victor X5, PerkinElmer). When tRNA-aptamer RNA was added to DFHBI, fluorescent intensity was about seven-fold higher to wells containing DFHBI alone, validating that the tRNA-aptamer RNA can bind to DFHBI and activate its green fluorescence (FIG. 6).

Several aptamer sequences, including some of which are exemplified herein, are listed in Table 5 below, where anticodons are shown in bold and aptamer sequences within modified tRNAs are underlined.

TABLE 5

Aptamer and fusion sequences.

| SEQ ID NO: | Title | Sequence |
|---|---|---|
| 1 | Spinach aptamer | GACGCGACTGAATGAAATGGTGAAGGACGGGTCCAGGT GTGGCTGCTTCGGCAGTGCAGCTTGTTGAGTAGAGTGT GAGCTCCGTAACTAGTCGCGTC |
| 2 | Spinach2 aptamer | GATGTAACTGAATGAAATGGTGAAGGACGGGTCCAGTA GGCTGCTTCGGCAGCCTACTTGTTGAGTAGAGTGTGAG CTCCGTAACTAGTTACATC |
| 3 | Broccoli aptamer | GAGACGGTCGGGTCCAGATATTCGTATCTGTCGACTAG AGTGTGGGCTC |
| 4 | Mango aptamer | GGAATATAAAGAAGGGACGGTGCGGAGAGGAGATTTAT ATT |
| 5 | V-Spinach tRNA$^{Tyr/CUA}$ | GGTGGGGTTCCCGAGCGGCCAAAGGGAGCAGACTCTAAATCTGCCGTCAC<u>GACGCGACTGAATGAAATGGTGAAGG ACGGGTCCAGGTGTGGCTGCTTCGGCAGTGCAGCTTGT TGAGTAGAGTGTGAGCTCCGTAACTAGTCGCGTCAGAC</u>TTCGAAGGTTCGAATCCTTCCCCCACCACCA |
| 6 | V-Spinach tRNA$^{Leu/CAG}$ | GCGAAGGTGGCGGAATTGGTAGACGCGCTAGCTTCAGGTGTTAGTGTCCTT<u>GACGCGACTGAATGAAATGGTGAAG GACGGGTCCAGGTGTGGCTGCTTCGGCAGTGCAGCTTG TTGAGTAGAGTGTGAGCTCCGTAACTAGTCGCGTCACG</u>GACGTGGGGGTTCAAGTCCCCCCCCTCGCACCA |

Example 7. In-Vivo Testing of Mammalian tRNA-Aptamers

Figure 7A:
FIG. 7A exhibits fluorescence of Hela cells transfected with a plasmid encoding tRNA$^{ser}$-Aptamer, in the presence of DFHBI.
Figure 7B:
FIG. 7B exhibits fluorescence of Hela cells transfected with a plasmid encoding tRNA$^{ser}$-Aptamer, in the presence of DFHBI.

To determine whether tRNA$^{ser}$-Aptamer could be used to follow tRNAs in living mammalian cells, human Hela cells were transfected with the mammalian expression tRNA-aptamer vector. Specifically, Hela cells were plated in 96-well glass-bottom plate (10,000 cells per well), 24 hours later, cells were transfected with plasmid encoding tRNAser-Aptamer (200 ng per well) with Turbofect reagent (Thermo). Twenty-four hours post transfections cells were washed in imaging medium (Thermo) and incubated in imaging medium or in imaging medium containing DFHBI (20 µM) and Hoechst (0.5 µg/ml) for nuclei imaging. Following incubation (30 min.) tRNA-Aptamer-DFHBI fluorescence was detected by high content microscopy (Operetta, PerkinElmer). Images were collected every 30 minutes, for 2 hours and tRNA$^{ser}$ fluorescence was detected. Fluorescence was observed throughout cells only when DFHBI was added (FIG. 7A) and not in the absence of DFHBI (FIG. 7B). Moreover, intense spots were detected in the cytoplasm, which may correlate with ribosomes.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A recombinant transfer RNA (tRNA) molecule consisting of a tRNA molecule and an aptamer fused to the tRNA molecule,
wherein the tRNA molecule has:
an acceptor stem, a D arm which includes a D stem and a D loop, an anticodon arm which includes an anticodon stem and an anticodon loop, a V loop, and a T arm which includes a T stem and a T loop;
wherein the aptamer is fused to the V loop of said tRNA molecule, is capable of binding to a signal-emitting ligand, and optionally has a target-binding module or a target-binding module and a transducer module; and
wherein the recombinant tRNA molecule is capable of participating in effective translation.

2. The recombinant tRNA molecule of claim 1, wherein the aptamer has the target-binding module, wherein said target-binding module is capable of binding to a target ligand.

3. The recombinant tRNA molecule of claim 1, wherein the aptamer has the target-binding module and the transducer module, wherein said transducer module functionally links the target-binding module to a ligand-binding module within said aptamer.

4. The recombinant tRNA molecule of claim 1, wherein the aptamer is bound to the signal-emitting ligand.

5. The recombinant tRNA molecule of claim 4, wherein the signal-emitting ligand emits a fluorescent signal.

6. The recombinant tRNA molecule of claim 1, wherein the aptamer has the oligonucleotide sequence set forth in any one of SEQ ID NO: 1, SEQ ID NO: 2, SEQ ID NO: 3, SEQ ID NO: 4, and derivatives thereof.

7. A recombinant transfer RNA (tRNA) molecule consisting of a tRNA molecule and an aptamer fused to the tRNA molecule,
wherein the tRNA molecule has:
an acceptor stem, a D arm which includes a D stem and a D loop, an anticodon arm which includes an anticodon stem and an anticodon loop, a V loop, and a T arm which includes a T stem and a T loop; and
a CCA tail;
wherein the aptamer is fused to the V loop of said tRNA molecule, is capable of binding to a signal-emitting ligand, and optionally has a target-binding module or a target-binding module and a transducer module; and
wherein the recombinant tRNA molecule is capable of participating in effective translation.

8. A recombinant transfer RNA (tRNA) molecule consisting of a tRNA molecule and an aptamer fused to the tRNA molecule,
wherein the tRNA molecule has:
an acceptor stem, a D arm which includes a D stem and a D loop, an anticodon arm which includes an anticodon stem and an anticodon loop, a V loop, and a T arm which includes a T stem and a T loop;
a CCA tail, and
an amino acid;
wherein the aptamer is fused to the V loop of said tRNA molecule, is capable of binding to a signal-emitting ligand, and optionally has a target-binding module or a target-binding module and a transducer module; and
wherein the recombinant tRNA molecule is capable of participating in effective translation.

9. A method of monitoring a recombinant tRNA molecule, comprising the steps of:
i. obtaining a recombinant tRNA molecule according to claim 1;
ii. contacting the recombinant tRNA molecule with a signal-emitting ligand capable of being bound by the aptamer of the tRNA molecule; and
iii. monitoring the signal emitted by the signal-emitting ligand; thereby monitoring the recombinant tRNA molecule.

10. The method of claim 9, further comprising monitoring an interaction between the recombinant tRNA molecule and an additional molecule.

11. The method of claim 10, wherein the interaction is selected from the group consisting of ribosomal activity, mRNA translation, protein synthesis, stress response in a cell, tissue or organ, level of tRNA, nucleoli localization in a cell and a tRNA-related disease.

12. The method of claim 11, comprising monitoring the tRNA-related disease, wherein the tRNA-related disease is associated with mutations in tRNA genes.

13. The method of claim 11, where the cell is an eukaryote cell.

14. The method of claim 9, wherein the method is performed in a cell.

15. The recombinant tRNA molecule of claim 6, wherein the aptamer has the oligonucleotide sequence set forth in SEQ ID NOs: 1 or 2.

16. The recombinant tRNA molecule of claim 6, wherein the aptamer has the oligonucleotide sequence set forth in SEQ ID NOs: 3 or 4.

17. The recombinant tRNA molecule of claim 6, consisting of the tRNA molecule and an aptamer fused to the tRNA molecule,
wherein the tRNA molecule has the acceptor stem, D arm which includes the D stem and D loop, the anticodon arm which includes the anticodon stem and anticodon loop, the V loop, and the T arm which includes the T stem and T loop;
wherein the aptamer is fused to the V loop of said tRNA molecule and has the oligonucleotide sequence set forth in SEQ ID NO: 1; and
wherein the recombinant tRNA molecule is capable of participating in effective translation.

18. The recombinant tRNA molecule of claim 6, consisting of the tRNA molecule and an aptamer fused to the tRNA molecule,
- wherein the tRNA molecule has the acceptor stem, D arm which includes the D stem and D loop, the anticodon arm which includes the anticodon stem and anticodon loop, the V loop, and the T arm which includes the T stem and T loop;
- wherein the aptamer is fused to the V loop of said tRNA molecule and has the oligonucleotide sequence set forth in SEQ ID NO: 2; and
- wherein the recombinant tRNA molecule is capable of participating in effective translation.

19. The recombinant tRNA molecule of claim 6, consisting of the tRNA molecule and an aptamer fused to the tRNA molecule,
- wherein the tRNA molecule has the acceptor stem, D arm which includes the D stem and D loop, the anticodon arm which includes the anticodon stem and anticodon loop, the V loop, and the T arm which includes the T stem and T loop;
- wherein the aptamer is fused to the V loop of said tRNA molecule and has the oligonucleotide sequence set forth in SEQ ID NO: 3; and
- wherein the recombinant tRNA molecule is capable of participating in effective translation.

20. The recombinant tRNA molecule of claim 6, consisting of the tRNA molecule and an aptamer fused to the tRNA molecule,
- wherein the tRNA molecule has the acceptor stem, D arm which includes the D stem and D loop, the anticodon arm which includes the anticodon stem and anticodon loop, the V loop, and the T arm which includes the T stem and T loop;
- wherein the aptamer is fused to the V loop of said tRNA molecule and has the oligonucleotide sequence set forth in SEQ ID NO: 4; and
- wherein the recombinant tRNA molecule is capable of participating in effective translation.

* * * * *